United States Patent [19]

Lee et al.

[11] Patent Number: 5,011,773

[45] Date of Patent: Apr. 30, 1991

[54] HUMAN ESTERASE D, ITS USES AND A PROCESS OF PURIFICATION

[75] Inventors: Wen-Hwa Lee; Eva Y-H.P. Lee, both of San Diego, Calif.

[73] Assignee: The Reagents of the University of California, Berkeley, Calif.

[21] Appl. No.: 91,547

[22] Filed: Aug. 31, 1987

[51] Int. Cl.$^5$ .................. C12P 21/06; C12P 21/04; C12P 19/34; C01N 15/00; C12H 15/12; C07K 3/00

[52] U.S. Cl. .................. 435/69.1; 435/71.2; 435/91; 435/172.3; 435/252.33; 435/320.1; 536/27; 530/350; 935/18; 935/29; 935/41; 935/48; 935/58; 935/62; 935/73; 935/82

[58] Field of Search .......... 435/68, 71, 91, 172.1, 435/172.3, 253, 320; 536/27; 530/350; 935/18, 23, 27, 31, 41, 73, 69.1, 71.2, 252.33

[56] References Cited

PUBLICATIONS

Friend, S. H. et al., Nature, vol. 323, pp. 643–646 (1986).
Lalande; M. et al, Canc. Genet. Cytogenet., vol. 13, pp. 283–295 (1984).
Helfman, D. M. et al, Proc. Nat'l Acad. Sci., U.S.A., vol. 80, pp. 31–35 (1983).

*Primary Examiner*—Robin L. Teskin
*Assistant Examiner*—Joan Ellis
*Attorney, Agent, or Firm*—Bernard L. Kleinke; William Patrick Waters; Jerry R. Potts

[57] ABSTRACT

This invention relates in general to a human esterases and in particular to the human esterase D enzyme and identification of its amino acid sequence, to a human esterase D cDNA and identification of its nucleotide sequence, to localization of the human esterase D gene and identification of its sequence, to specific human esterase D antibodies and to a method of purifying esterase D. The present invention also relates to using the cloned human esterase D cDNA as a genetic marker and a diagnostic tool for retinoblastoma, Wilson's disease and other hereditary or acquired diseases controlled by genes located at the 13 chromosome 13q14 region. The invention further relates to an esterase D cDNA probe for cloning the retinoblastoma gene and to the use of the cloned human esterase cDNA as a prognostic tool for determination of genetic predisposition to retinoblastoma or Wilson's disease and for population screening. Finally, this invention relates to the use of the cloned human esterase D for exploration of the large family of human esterases.

11 Claims, 13 Drawing Sheets

| | | | | | | | | | | | |
|---|---|---|---|---|---|---|---|---|---|---|---|
| 1 | GAA | TTC | CGG | CGG | CCA | TCT | TGA | GCC | CCT | TTT | ACT | TCG | GCC | CGC | TTC | TTC | TGG | TCA | | 60 |
| 61 | CTC | CGC | CTC | CGT | AGA | ATC | GCC | TAC | TTG | CAA | GTG | GCA | AAA | AGC | CAG | AAT | CAG | TTG | GAC | 120 |
| 121 | AGG | AAA | AGA | AGA | ATG | GCA | TTG | AAG | CAG | ATT | TCC | AAC | AAG | TGC | TTT | GGG | GGA | TTG | CAG | AAA |180 |
| 1 | | | | | Met | Ala | Leu | Lys | Gln | Ile | Ser | Asn | Lys | Cys | Phe | Gly | Gly | Leu | Gln | Lys | 17 |
| 181 | GTT | TTT | GAA | CAT | GAC | AGT | GTT | GAA | CTA | AAC | TGC | AAA | ATG | TTT | GCT | GTC | TAC | TTA | CCA | 240 |
| 18 | Val | Phe | Glu | His | Asp | Ser | Val | Glu | Leu | Asn | Cys | Lys | Met | Phe | Ala | Val | Tyr | Leu | Pro | 37 |
| 241 | CCA | AAG | GCA | GAA | ACA | GGA | AAG | TGC | CCT | GCA | CTG | TAT | TGG | CTC | TCA | GGT | TTA | ACT | TGC | ACA | 300 |
| 38 | Pro | Lys | Ala | Glu | Thr | Gly | Lys | Cys | Pro | Ala | Leu | Tyr | Trp | Leu | Ser | Gly | Leu | Thr | Cys | Thr | 57 |
| 301 | GAG | CAA | AAT | TTT | ATA | TCA | AAA | TCT | GGT | TAT | CAT | CAG | TCT | GCT | TCA | GAA | CAT | GGT | CTT | GTT | 360 |
| 58 | Glu | Gln | Asn | Phe | Ile | Ser | Lys | Ser | Gly | Tyr | His | Gln | Ser | Ala | Ser | Glu | His | Gly | Leu | Val | 77 |
| 361 | GTC | ATT | GCT | CCA | GAT | ACC | AGC | CCT | CGT | GGC | TGC | AAT | ATT | AAA | GGT | GAA | GAT | GAG | AGC | TGG | 420 |
| 78 | Val | Ile | Ala | Pro | Asp | Thr | Ser | Pro | Arg | Gly | Cys | Asn | Ile | Lys | Gly | Glu | Asp | Glu | Ser | Trp | 97 |
| 421 | GAC | TTT | GGC | ACT | GGT | GCT | GGA | TTT | TAT | GTT | GAT | GCC | ACT | GAA | CCT | TGG | AAA | ACC | AAC | 480 |
| 98 | Asp | Phe | Gly | Thr | Gly | Ala | Gly | Phe | Tyr | Val | Asp | Ala | Thr | Glu | Pro | Trp | Lys | Thr | Asn | 117 |
| 481 | TAC | AGA | ATG | TAC | TCT | TAT | GTC | ACA | GAG | GAG | CTT | CCC | CAA | CTC | ATA | AAT | GCC | AAT | TTT | CCA | 540 |
| 118 | Tyr | Arg | Met | Tyr | Ser | Tyr | Val | Thr | Glu | Glu | Leu | Pro | Gln | Leu | Ile | Asn | Ala | Asn | Phe | Pro | 137 |
| 541 | GTG | GAT | CCC | CAA | AGG | ATG | TCT | ATT | TTT | GGC | CAC | ATG | GGA | GGT | CAT | GGA | GCT | CTG | ATC | 600 |
| 138 | Val | Asp | Pro | Gln | Arg | Met | Ser | Ile | Phe | Gly | His | Met | Gly | Gly | His | Gly | Ala | Leu | Ile | 157 |

FIG. 7

| | | | | | | | | | | |
|---|---|---|---|---|---|---|---|---|---|---|
| 601<br>158 | TGT<br>Cys | GCT<br>Ala | TTG<br>Leu | AAA<br>Lys | AAT<br>Asn | CCT<br>Pro | GGA<br>Gly | AAA<br>Lys | TAC<br>Tyr | AAA<br>Lys | TCT<br>Ser | GTG<br>Val | TCA<br>Ser | GCA<br>Ala | TTT<br>Phe | GCT<br>Ala | CCA<br>Pro | ATT<br>Ile | TGC<br>Cys | AAC<br>Asn | 660<br>177 |
| 661<br>178 | CCT<br>Pro | GTA<br>Val | CTC<br>Leu | TGT<br>Cys | CCC<br>Pro | TGG<br>Trp | GGC<br>Gly | AAA<br>Lys | GCC<br>Ala | TTT<br>Phe | AGT<br>Ser | GGA<br>Gly | TAT<br>Tyr | TTG<br>Leu | GGA<br>Gly | ACA<br>Thr | GAT<br>Asp | CAA<br>Gln | AGT<br>Ser | 720<br>197 |
| 721<br>198 | AAA<br>Lys | TGG<br>Trp | AAG<br>Lys | GCT<br>Ala | TAT<br>Tyr | GAT<br>Asp | CAC<br>His | ACC<br>Thr | GCT<br>Ala | CTT<br>Leu | GTG<br>Val | AAA<br>Lys | TCC<br>Ser | TAT<br>Tyr | CCA<br>Pro | TCT<br>Ser | CAG<br>Gln | CTG<br>Leu | GAC<br>Asp | 780<br>217 |
| 781<br>218 | ATA<br>Ile | CTA<br>Leu | ATT<br>Ile | GAT<br>Asp | CAT<br>His | AGC<br>Ser | CAA<br>Gln | CAG<br>Gln | TTT<br>Phe | CTT<br>Leu | TTA<br>Leu | GAT<br>Asp | GAC<br>Asp | GAT<br>Asp | GGA<br>Gly | CAG<br>Gln | TTA<br>Leu | CTC<br>Leu | CCT<br>Pro | GAT<br>Asp | 840<br>237 |
| 841<br>238 | AAC<br>Asn | TTC<br>Phe | ATA<br>Ile | GCT<br>Ala | GCC<br>Ala | TGT<br>Cys | ACA<br>Thr | GAA<br>Glu | AAG<br>Lys | GCC<br>Ala | CGT<br>Arg | GTT<br>Val | TTT<br>Phe | CGA<br>Arg | TTG<br>Leu | CAA<br>Gln | CAT<br>His | GAG<br>Glu | GGT<br>Gly | 900<br>257 |
| 901<br>258 | TAT<br>Tyr | GAT<br>Asp | CAT<br>His | AGC<br>Ser | TAC<br>Tyr | TAC<br>Tyr | TTC<br>Phe | ATT<br>Ile | GCA<br>Ala | ACC<br>Thr | TTT<br>Phe | ATT<br>Ile | ACT<br>Thr | GAC<br>Asp | CAC<br>His | ATC<br>Ile | AGA<br>Arg | CAT<br>His | CAT<br>His | GCT<br>Ala | 960<br>277 |
| 961<br>278 | AAA<br>Lys | TAC<br>Tyr | CTG<br>Leu | AAT<br>Asn | GCA<br>Ala | TGA<br>--- | AAA<br>--- | AAC<br>--- | TCC<br>--- | AAA<br>--- | TAA<br>--- | GAG<br>--- | AAT<br>--- | CTC<br>--- | TTC<br>--- | AGG<br>--- | ATT<br>--- | ATA<br>--- | AAA<br>--- | GTT<br>--- | 1020 |
| 1021 | GTA | AAA | TGC | AAC | TGT | ATT | GCT | GAG | CAA | AAA | AAA | AAA | TTC | AAA | ACA | TTG | GAT | TTT | ATA | 1080 |
| 1081 | GTG | CTA | AAA | GGG | CTT | TAT | TCT | ATA | GTT | GAA | TCA | CCT | CTG | AAT | AAA | GAT | ATA | AAA | CCT | AAA | 1140 |
| 1141 | AAA | ACC | CGA | ATT | C | | | | | | | | | | | | | | | | |

FIG. 7 (Continued)

|     |     |     |     |     |     |     |     |     |     |     |     |     |     |
| --- | --- | --- | --- | --- | --- | --- | --- | --- | --- | --- | --- | --- | --- |
| 1   | GAA | TTC | GGG | GCA | AAA | AGC | AAT | CAG | CAA | TTG | EAC | AGG | AAA AGA ATG |
|     | Glu | Phe | Gly | Ala | Lys | Ser | Asn | Gln | Gln | Leu | Asp | Arg | Lys Arg Met |
| 91  | AAA | GTT | TTT | GAA | CAT | GAC | AGT | GTT | GAA | CTA | AAC | TGC | AAA ATG AAA |
|     | Lys | Val | Phe | Glu | His | Asp | Ser | Val | Glu | Leu | Asn | Cys | Lys Met Lys |
| 181 | GCA | TGT | ATT | GGC | TCT | CCA | GGT | TTA | ACT | TGC | ACA | GAG | CCA AAA TTT |
|     | Ala | Cys | Ile | Gly | Ser | Pro | Gly | Leu | Thr | Cys | Thr | Glu | Pro Lys Phe |
| 271 | TCT | TGT | TGT | CAT | TGC | TCC | AGA | TAC | AGC | CCT | CGT | GCG | TGC AAT ATT |
|     | Ser | Cys | Cys | His | Cys | Ser | Arg | Tyr | Ser | Pro | Arg | Ala | Cys Asn Ile |
| 361 | TAT | GTT | GAT | GCC | ACT | GAA | GAT | CCT | TGG | AAA | ACC | AAC | TAC AGA ATG |
|     | Tyr | Val | Asp | Ala | Thr | Glu | Asp | Pro | Trp | Lys | Thr | Asn | Tyr Arg Met |
| 451 | TTT | CCA | GTG | GAT | CCC | CAA | AGG | ATG | TCT | ATT | TTT | GGC | CAC TCC ATG |
|     | Phe | Pro | Val | Asp | Pro | Gln | Arg | Met | Ser | Ile | Phe | Gly | His Ser Met |
| 541 | TAC | AAA | TCT | GTG | TCA | GCA | TTT | GCT | CCA | ATT | TGC | AAC | CCT GTA CTC |
|     | Tyr | Lys | Ser | Val | Ser | Ala | Phe | Ala | Pro | Ile | Cys | Asn | Pro Val Leu |
| 631 | CAA | AST | AAA | TGG | AAG | GCT | TAT | GAT | GCT | ACC | CAC | CTT | GTG AAA TCC |
|     | Gln | Ser | Lys | Trp | Lys | Ala | Tyr | Asp | Ala | Thr | His | Leu | Val Lys Ser |
| 721 | GAC | CAG | TTT | CTT | TTA | GAT | GGA | CAG | TTA | CTC | CCT | GAT | AAC TTC ATA |
|     | Asp | Gln | Phe | Leu | Leu | Asp | Gly | Gln | Leu | Leu | Pro | Asp | Asn Phe Ile |
| 811 | GAG | GGT | TAT | GAT | CAT | AGC | TAC | TAC | TTC | ATT | GCA | ACC | TTT ATT ACT |
|     | Glu | Ely | Tyr | Asp | His | Ser | Tyr | Tyr | Phe | Ile | Ala | Thr | Phe Ile Thr |
| 901 | TCC | AAA | TAA | GAG | AAT | CTC | TTC | AGG | ATT | ATA | AAA | GTT | GTA AAA TGC |
| 991 | TTT | ATG | GTG | CTA | AAA | GGG | CTT | TAT | TCT | ATA | GTT | GAA | TCA CCT CTG |

FIG. 8

```
GCA TTG AAG CAG ATT TCC AGC AAC AAG TGC TTT GGG GGA TTG CAG      90
Ala Leu Lys Gln Ile Ser Ser Asn Lys Cys Phe Gly Gly Leu Gln

TTT GCT GTC TAC TTA CCA CCA AAG GCA GAA ACA GGA AAG TGC CCT     180
Phe Ala Val Tyr Leu Pro Pro Lys Ala Glu Thr Gly Lys Cys Pro

III
TAT CAT CAA AAT CTG GTT ATC ATC AGT CTG CTT CAG AAC CAT TTG     270
Tyr His Gln Asn Leu Val Ile Ile Ser Leu Leu Gln Asn His Leu

AAA GGT GAA GAT GAG AEC TGG GAC TTT GCG ACT GGT CGT GGA TTT     360
Lys Gly Glu Asp Glu Ser Trp Asp Phe Ala Thr Gly Arg Gly Phe

TAC TCT TAT GTC ACA GAG GAG CTT CCC CAA CTC ATA AAT GCC AAT     450
Tyr Ser Tyr Val Thr Elu Elu Leu Pro Gln Leu Ile Asn Ala Asn

II
GGA GGT CAT GGA GCT CTG ATC TGT GCT TTG AAA AAT CCT GGA AAA     540
Gly Gly His Gly Ala Leu Ile Cys Ala Leu Lys Asn Pro Gly Lys

IV
TGT CCC TGG GGC AAA AAA GCC TTT AGT GGA TAT TTG GGA ACA GAT     630
Cys Pro Trp Gly Lys Lys Ala Phe Ser Gly Tyr Leu Gly Thr Asp

TAT CCA GGA TCT CAG CTG GAC ATA CTA ATT GAT CAA GGG AAA GAT     720
Tyr Pro Ely Ser Gln Leu Asp Ile Leu Ile Asp Gln Gly Lys Asp

GCT GCC TGT ACA GAA AAG AAA ATC CCC GTT GTT TTT CGA TTG CAA     810
Ala Ala Cys Thr Glu Lys Lys Ile Pro Val Val Phe Arg Leu Gln

GAC CAC ATC AGA CAT CAT GCT AAA TAC CTG AAT GCA TGA AAA AAC     900
Asp His Ile Arg His His Ala Lys Tyr Leu Asn Ala ---

AAC TGT ATT GCT GAG CAA AAA AAA AAA AAA TTC AAA ACA TTG GAT     990
AAT AAA GAT ATA AAA CCT AAA AAA ACC CGA ATT C     1069 /
```

FIG. 8 (Continued)

```
  1     Met Ala Leu Lys Gln Ile Ser Ser Asn Lys Cys Phe Gly Gly Leu Gln Lys   17
 18 Val Phe Glu His Asp Ser Val Glu Leu Asn Cys Lys Met Lys Phe Ala Val Tyr Leu Pro  37
 38 Pro Lys Ala Glu Thr Gly Lys Cys Pro Ala Leu Tyr Trp Leu Ser Gly Leu Thr Cys Thr  57
 58 Glu Gln Asn Phe Ile Ser Lys Ser Gly Tyr His Gln Ser Ala Ser Glu His Gly Leu Val  77
 78 Val Ile Ala Pro Asp Thr Ser Pro Arg Gly Cys Asn Ile Lys Gly Glu Asp Glu Ser Trp  97
 98 Asp Phe Gly Thr Gly Ala Gly Phe Tyr Val Asp Ala Thr Glu Lys Asp Pro Trp Lys Thr Asn 117
118 Tyr Arg Met Tyr Ser Tyr Val Thr Glu Leu Pro Gln Leu Ile Asn Ala Asn Phe Pro 137
138 Val Asp Pro Gln Arg Met Ser Ile Phe Gly His Ser Met Gly Gly His Gly Ala Leu Ile 157
158 Cys Ala Leu Lys Asn Pro Gly Lys Tyr Lys Ser Val Ser Ala Phe Ala Pro Ile Cys Asn 177
178 Pro Val Leu Cys Pro Trp Gly Lys Lys Ala Phe Ser Gly Tyr Leu Gly Thr Asp Gln Ser 197
198 Lys Trp Lys Ala Tyr Asp Ala Thr His Leu Val Lys Ser Tyr Pro Gly Ser Gln Leu Asp 217
218 Ile Leu Ile Asp Gln Gly Lys Asp Asp Gln Phe Leu Leu Asp Gln Phe Leu Gln Leu Pro Asp 237
238 Asn Phe Ile Ala Ala Cys Thr Glu Lys Lys Ile Pro Val Val Phe Arg Leu Gln Glu Gly 257
258 Tyr Asp His Ser Tyr Tyr Phe Ile Ala Thr Phe Ile Thr Asp His Ile Arg His His Ala 277
278 Lys Tyr Leu Asn Ala ---
```

FIG. 9

HUMAN ESTERASE D, ITS USES AND A PROCESS OF PURIFICATION

FIELD OF THE INVENTION

This invention relates in general to human esterases. The invention more particularly relates to the human esterase D enzyme and identification of its amino acid sequence, to a human esterase D cDNA and identification of its nucleotide sequence, to localization of the human esterase D gene and identification of its sequence, to specific human esterase D antibodies, and to a method of purifying esterase D. The present invention also relates to using the cloned human esterase D cDNA as a genetic marker, as well as a diagnostic tool for retinoblastoma, Wilson's disease and other hereditary or acquired diseases controlled by genes located at the chromosome 13q14:11 region. The invention further relates to an esterase D cDNA probe for cloning the retinoblastoma gene and to the use of the cloned human esterase cDNA as a prognostic tool for determination of genetic predisposition to retinoblastoma or Wilson's disease and for population screening. Finally, this invention relates to the use of the cloned human esterase D for exploration of the large family of human esterases.

"This invention was made with Government support under Grant No.: EY 05758 with the National Institutes of Health and the University of California. The Government has certain rights in this invention."

BACKGROUND

Esterases belong to the family of nonspecific enzymes that catalyze the hydrolysis of esters. Human esterase D (ESD) is one member of the esterase family distinguishable by its electrophoretic mobility and its relative specificity for methylumbelliferyl esters as substrate. Human ESD is the dimeric enzyme in that it displays several phenotypes as a result of the expression of codominant autosomal alleles, primarily allele ESD 1 and ESD 2. Such polymorphic nature of human ESD has been shown to be available marker in studies of population genetics. Am. Hum. Genet., 39: 1-20 (1975).

The activity of ESD enzyme depends on the normal function of the ESD gene. Consequently, absence, complete or partial inactivation, deletion of one ESD allele, mutation or other alterations in ESD sequences will result in decreasing of ESD activity. For example, the tissues of individuals with a deletion of one chromosome 13 show only 50% of the ESD activity of that found in the healthy individuals possessing a normal set of two chromosomes 13. Science, 219:973-975 (1983).

The genetic locus of ESD was mapped to the chromosome 13q14:11 region by correlating the loss of enzyme activity with deletions on chromosome 13. Science, 208:1042-1044 (1980). The regional assignment of ESD to 13q14:11 region coincides with the location of the retinoblastoma (RB) gene, shown to be involved in the tumorigenesis of retinoblastoma. Am. J. Dis. Child., 132:161-163 (1978); Science, 219:973-975; Science, 213:1501-1503 (1981). The development of homozygosity or hemizygosity in the 13q14 region by deletion, mitotic recombination, or chromosomal loss has been interpreted as a primary event in retinoblastoma. This finding is consistent with the hypothesis that inactivation of both alleles of a gene located at 13q14:11 is required for tumorigenesis.

By examining levels of esterase D mapping to 13q14:11, it was previously inferred that one chromosome 13 in the somatic cells of the retinoblastoma patient contained a submicroscopic deletion of the RB and esterase D loci and that this chromosome was retained in her tumor, while the normal chromosome 13 was lost. Cancer Gen. Cytogen, 6:213-221 (1982).

Retinoblastoma is a malignant tumor of the sensory layer of the retina. The neoplastic tumor is composed of primitive retinal cells, occurring either bilaterally or unilaterally, usually before the third year of life. Retinoblastomas are characterized by small round cells with deeply staining nuclei, and elongated cells forming rosettes. They cause death by usually local invasion, especially along the optic nerves.

The molecular mechanism of the formation of this tumor is unknown. Absence or inactivation of the RB gene is believed to be the primary cause of this inheritable, childhood cancer. Science, 213:1501-1503 (1981); Science, 223: 1028-1033 (1984); Proc. Natl. Acad. Sci., 68:820-823 (1971); Nature, 305:779-784 (1980). Since little of the RB gene structure or function is known, its cloning proved to be difficult. Discover, March:95-96 (1987). The difficulties with cloning of the RB gene were similar to that encountered in cloning the muscular dystrophy or the cystic fibrosis genes. Nature, 316:842-845 (1985), Science, 230:1054-1057 (1985).

The latest reports indicate that the RB gene has a regulatory function and that its presence and normal function prevents the development of the retinoblastoma. On the other hand, absence, malfunctioning or inactivation of the RB gene causes the development of, or genetical predisposition and susceptibility to, the retinoblastoma and is believed to be the primary cause for both hereditary and acquired retinoblastoma, and for the secondary malignancies often recurring in retinoblastoma patients such as osteosarcoma, and fibrosarcoma.

Therefore, to find the way how to determine the genetic predisposition in fetus or the susceptibility to acquire retinoblastoma in later age is of utmost importance for early diagnosis and/or possible treatment through a genetic manipulation.

The localization of the ESD and RB genes in the same chromosomal region provides an advantageous approach for evaluation of the RB gene functioning, for discovery of RB chromosomal patterns and for cloning of the RB gene using the ESD as the starting point. Science, 235:1394-1399 (1987). The tight linkage between these two genes allows the ESD gene to serve as a crucial marker in elucidating the behavior of the RB gene. Science, 219:973-975 (1982); and Nature, 304:451-453 (1983).

Thus, the identified and cloned ESD cDNA would be advantageous in the identification of the RB gene location which in turn would allow RB diagnosis and treatment.

Besides the RB gene, the defective gene in Wilson's disease has been found to be located in the same chromosomal region 13q14:11, and thus was found to be linked to the ESD gene. Proc. Natl. Acad. Sci., 82:1819-1821 (1985). Wilson's disease, also known as hepatolenticular degeneration, is an hereditary disease of ceruloplasmin formation transmitted as an autosomal recessive. It is characterized by gross reduction in the incorporation of copper in ceruloplasmin resulting in decreased serum ceruloplasmin and copper values, and increased excretion of copper in the urine. The close linkage found between Wilson's disease locus and the ESD gene, which can serve as the polymorphic marker for Wilson's disease, has the profound implications both for investigation of the primary gene defect and for clinical use.

The identified and cloned ESD cDNA thus would provide a valuable marker in the identification of the Wilson's disease gene and would lead, eventually, to diagnosis and treatment of this inheritable genetic disease.

In addition to serving as a genetic marker for retinoblastoma and Wilson's disease, the ESD may play a role in detoxification. It has been recently observed that the ESD protein is distributed at the highest level in liver and kidney and that it is inducible by phenobarbital, but not phorbol myristate ester treatment. *Proc. Nat. Acad. Sci.*, 83:6790–6794 (1986).

Although the esterase D has been found in most tissues, not much is known about its structure and function. A protocol for partial purification of this enzyme has been described previously but the purity achieved by the procedure was only 30%—40%. *Am. J. Hum. Genet.*, 30,14–18 (1978). Thus, it remains difficult to obtain a sufficient amount of the purified, homogeneous enzyme to generate specific anti-esterase D antibodies.

It would be, therefore, valuable to obtain a highly purified form of human ESD and to develop a method of preparing such highly purified human ESD protein. Further, it would be desirable to prepare specific anti-esterase D antibodies, and to isolate a human ESD cDNA clone, to identify the human ESD cDNA and ESD gene nucleotide sequence and human ESD amino acid sequence.

It is therefore one object of this invention to provide a purified human ESD and to determine its amino acid sequence.

It is another object of the present invention to provide a process for purifying human ESD.

It is yet another object of this invention to provide a specific polyclonal antibody against a purified human ESD.

It is still another object of the invention to provide the human ESD cDNA and to determine its nucleotide sequence.

It is still another object of the invention to clone ESD cDNA and to isolate and construct the ESD cDNA probes.

It is a further object of the present invention to provide a human ESD cDNA radioactive probe which can be utilized as a genetic marker for retinoblastoma and Wilson's disease.

It is still a further object of this invention to identify and isolate human ESD gene and to determine its nucleotide sequence.

DETAILED DESCRIPTION OF THE INVENTION

Since the genetic locus involved in the genesis of retinoblastoma is tightly linked to the esterase D gene, it is very crucial to clone the esterase D gene. The availability of the completely sequenced cDNA clone and ESD gene will facilitate future retinoblastoma studies.

Recently, the human esterase D was successfully purified. The polyclonal anti-esterase D antibody was prepared, and oligonucleotide probes complementary to certain ESD peptides were constructed. The complete amino acid sequence of ESD protein was determined, and ESD cDNA was cloned. The complete nucleotide sequence of ESD cDNA and the amino acid sequence of ESD protein were identified and the ESD gene was localized.

Since all convenient approaches for cloning the esterase D gene required a significant amount of the purified protein, the presence, localization and purification of the ESD were first examined.

The presence of the esterase D protein was examined in cells from different species of mammals such as mouse NIH 3T6 fibroblasts, rat-2 fibroblasts, Chinese hamster ovarian cells, the COS cell line of monkey fibroblasts, and a human premonocytic cell line (U937). When these tissues were labelled with [$^{35}$S]methionine and immunoprecipitated with the rabbit polyclonal IgG, a single polypeptide, later identified as the ESD, with a molecular mass of 33–34 kDa, was found in all species. Enzymatic activity associated with the immunoprecipitates derived from these cell lines indicate that ESD enzyme is present and conserved in mammals through the evolution, suggesting its important physiological function.

Tissue distribution of ESD activity has shown that liver and kidney contain 10-fold higher enzymatic activity than blood, spleen, heart, lung, muscle, brain, mammary glands and intestine. These results imply that esterase D might play a role in detoxification. The fact that a group of nonspecific esterases in the livers of rats and rabbits could be induced by phenobarbital treatment supports this notion. *Biochem. Biophys. Acta.*, 582: 185:195 (1979); and *Arch. Biochem. Biophys.*, 181: 534–541 (1977). An observation of a 3-fold increase of synthesis of esterase D protein in cultured U937 cells upon treatment of 0.1 mM phenobarbital further substantiates this contention.

In human tissues, there are at least eight or nine different nonspecific esterases. *Am. Hum. Genet.*, 39:1–20 (1975). Until now, purification of any specific esterase has been hampered because of the lack of a specific assay. However, esterase D has been shown to hydrolyze 4-methylumbelliferyl acetate in a somewhat specific manner, and therefore at least a partial purification of this enzyme has been possible and has been reported. Nevertheless, all attempts to purify this protein by following the published protocol only resulted in an enzyme purity of 30-40%.

In contrast, the current protocol of several purification steps including three consequent column chromatography separations (FIG. 1A), described in Example 1, for purifying human esterase D from outdated erythrocytes, resulted in a 10,000-fold purification with at least a 13% yield of activity (Table 1). The actual yield may be even higher, because samples obtained in the early steps of the purification may contain some other esterases that also act on 4-methylumbelliferyl acetate. The purified human esterase D finally obtained behaved as a single band in NaDodSO$_4$/PAGE stained either with Coomassie blue or silver, suggesting that the enzyme was biochemically homogeneous (FIG. 1B). Among the large family of human esterases, only esterase D, in addition to the esterase B$_4$ described in *Eur. J. Biochem.*, 61:331–335 (1976), has been purified to this degree. Interestingly, another esterase, esterase X, with a molecular mass of 30 kDa, was also partially purified by this protocol (FIG. 1B).

The current invention provides a process of purifying human ESD by first obtaining the human ESD from human tissue, lysing said tissue, extracting the lysed tissue with an organic solvent, partially purifying the extract and then separating the purified ESD by column chromatography.

The purified human ESD obtained above was subsequently used in the preparation of specific rabbit anti-esterase antibody.

The specific rabbit polyclonal antibody against esterase D (IgG) were prepared by the procedure described in Example 2. Rabbit polyclonal antibody were obtained by injecting rabbits with purified ESD mixed with the complete Freund's adjuvant followed with booster injections of purified esterase D protein in admixture with incomplete Freund's adjuvant for several months until the titer of antibody was sufficiently high to specifically immunoprecipitate the ESD protein.

The titer of antibody was followed by immunoblotting analysis described in *Proc. Natl. Acad. Sci.,* 76:4350–43354 (1979). When the sufficiently high titer of specific anti-esterase D antibody was obtained, it was purified by column chromatography, preferably by protein A Sepharose column, and used in immunological identification of the purified ESD in various animal species.

The above obtained specific human anti-esterase D antibody was able to bind a polypeptide with a molecular mass of about 33–34 kDa subsequently identified as ESD.

Using this new rabbit anti-esterase D antibody, a protein corresponding to human esterase D from mouse, rat, hamster, and monkey cells was immunoprecipitated. This supported the previous findings that esterase D is highly conserved in evolution and may subserve a critical physiological function.

The above described immunological reaction was then used in identification and the isolation of the ESD cDNA clones from two λgtll cDNA libraries. The technique which was used is described in *Proc. Natl. Acad. Sci.,* 80:1194–1198 (1983) and was devised for purposes of cloning genes by using specific antibody as probes and for isolating unknown proteins encoded by cloned DNA. In general, the method uses an expression vector, λgtll (lac5 nin5 cI857 S 100) that permits insertion of foreign DNA into β-galactosidase structural gene lac Z and promotes synthesis of hybrid fusion proteins, *DNA,* 3:437–447(1984).

It was presumed that since the ESD was shown to be present in many tissues, the mRNA coding for ESD will be readily present in tissue extracts and/or in certain tissue tumors. Human hepatoma and human placenta tumors both have a relatively high level of expression of ESD mRNA and were, therefore, particularly suitable for the detection of specific ESD cDNA clones in the library. Therefore, these two tumors were chosen for constructing the ESD cDNA libraries in λgtll vector.

Two λgtll cDNA libraries constructed using human hepatoma mRNA according to procedure described in *DNA,* 3:437–447 (1984) and human placenta mRNA according to procedure in *J. Biol. Chem.,* 262:3112–3115 (1986), respectively, were plated on E. coli strain Y1090 and screened according to procedure described in *Proc. Natl. Acad. Sci.,* 80:1194–1198 (1983). After 3–5 hours of incubation at 42° C., the bacterial lawns were covered with a 137-mm nitrocellulose filter soaked in 10 mM isopropyl β-D-thiogalactoside and dried. Incubation was continued but shifted to 37° C. for 5 hours. The filters were first soaked with 3% nonfat dry milk and then incubated with the prepared anti-esterase D IgG at a concentration of 1 μg/ml overnight. After briefly washing with 1% Nonidet P-40, filters were incubated for 2 hours with $^{125}$I-labeled protein A, washed and dried. XAR-5 film was exposed to the filters overnight at $-80°$ C. using an intensifying screen. Positive phages were picked and repeatedly rescreened at lower density until a pure population was obtained.

Following the immunoscreening of these libraries with anti-esterase D antibody, four clones were obtained. Two smaller clones had the size of only 150–200 base pairs (bp). The other two clones, with identical 1.1 kb (1100 bp) inserts, were called EL22a and EL22b. These clones were then used in detection of fusion proteins as described in Example 5.

In this system positive clones detected by autoradiography, EL22a and EL22b, lysogenized in E. coli Y1090 and induced to express β-galactosidase fusion protein. The recombinant protein was produced that is a fusion of β-galactosidase and EL22 encoded by the adjoining cDNA (FIG. 5). The recombinant β-galactosidase/EL22 fusion protein of 145 kDa was detected by rabbit anti-esterase D IgG immunoblotting, according to the procedure described in Example 5.

The molecular mass of the β-galactosidase protein is known to 114 kDa and therefore, the remaining fragment of $\approx 31$ kDa was presumed to be encoded by ESD (EL22a or EL22b) fragments. The size of this fragment was smaller than the complete ESD protein, the insert therefore contained only approximately 90% of the sequence of the ESD protein. The complete ESD protein is known to have a molecular mass of 34 kDa.

The fragments of EL22a and EL22b were then hybridized with $^{32}$P-labeled 23-mer oligomeric probe as follows: DNA from recombinants λEL22a and EL22b were digested with restriction endonuclease EcoRI and electrophoresed through a 0.8% agarose gel. The digested fragments were transferred onto a nitrocellulose filter and hybridized with a $^{32}$P-labeled 23-mer oligonucleotide probe (infra) to give a labeled $^{32}$P DNA fragment of 1.1 kb detectable by XAR-5 film.

Synthetic oligonucleotide probes were constructed according to the procedure described in Example 4. In general, the purified ESD protein was cleaved with a chemical reagent, such as cyanogen bromide (CNBr), and the profile of CNBr-cleaved ESD protein was determined by reversed phase HPLC. The eluted polypeptides were dried, their amino acid sequences determined by solid-phase Edman degradation with HPL analysis of the phenylthiohydanton according to the procedure described in *Microcharacterization of Polypeptides: A Practical Manual,* ed. J. E. Shively, Humana, Clifton, N.J. (1985).

CNBr-cleaved ESD resulted in four polypeptides of various lengths. The nucleotide sequences corresponding to amino acid sequences of these polypeptides were determined and used to construct synthetic oligonucleotide probes. The probes were synthesized on a synthesizer using phosphotriester chemistry. Three sets of oligonucleotide mixtures corresponding to possible coding sequences of each peptide were constructed. The mixtures were purified on polyacrylamide/urea gels and labeled at the 5' end with $[\gamma-^{32}P]$ATP by using T4 polynucleotide kinase.

The molecular cloning of the human esterase D gene was done according to the protocol of Example 5 and its sequence determined according to Example 6.

DNA sequencing was done in general according to methods described in *Plasmid,* 13:31–46(1985); and *Proc. Natl. Acad. Sci.,* 74:5463–5467(1977). The λEL22 clone containing a 1100 basepair EcoRI insert was subcloned into M13 mp11 at the EcoRI site. The single-stranded DNAs of two recombinants with opposite orientation were isolated and used to construct 3' deletion mutants. Five mutants with different lengths of insert from each parental clone were sequenced by using the dideoxynucleotide chain termination method. As can be seen from FIG. 7, approximately 95% of the double-stranded DNA was sequenced. A long open reading frame encoding a protein of 31 kDa was found indicating the presence of a structural gene. The three stretches of amino acids sequences of peptides obtained previously from ESD protein cleaved with CNBr, were identically matched to the deduced protein sequences. These stretches are shown underlined in FIG. 7. Based on these findings, the conclusion was reached that EL22 clone is, in fact, the esterase D cDNA.

To determine the size of ESD mRNA, RNA blotting analysis was performed according to the method described in *Molecular Cloning: A Laboratory Manual*, Cold Spring Harbor Laboratory, Cold Spring Harbor, N.Y. (1982).

Cellular mRNA was prepared by the guanidine isothiocyanate/cesium chloride method and enriched by oligo(dT)-Sepharose column chromatography. Poly (A)-enriched mRNA was prepared from two cell lines, Y79 and LA-N-5 (*Nature*, 309: 458–460(1984)) and electrophoresed on 1.2% agarose containing formaldehyde and transferred to a nitrocellulose filter. The mRNA blot (1.3–1.4 kb) was hybridized with $^{32}$P-labeled pUCEL22 DNA probe as shown in FIG. 6A. The size of mRNA of the two cell lines was found to be $\approx 14,5S(1.3-1.4 \text{ kb})$.

A distribution of the ESD gene in the human genome was determined by Southern genomic blotting analysis using $^{32}$P-labeled EL22 clone according to procedure of *Molecular Cloning: A Laboratory Manual* (Supra).

DNA was extracted from normal peripheral blood lymphocytes, from Chinese hamster-human hybrid cells containing human chromosomes 13, 12 and the short arm of chromosome 6, GM1142, GM2718, GM3887 and Y79 cells. Y79 and Chinese hamster-human hybrid cells were obtained as described in *Nature*, 309:458–460(1984) and *Cytogenet Cell Genet.*, 28:116–120(1980) respectively.

Extracted DNA was completely digested with endonuclease EcoRI and subjected to electrophoresis on a 0.8% agarose gel. DNA fragments were analyzed by Southern genomic blotting. Genomic blots were hybridized with $^{32}$P-labeled EL22 cDNA clone as described previously. All investigated cells have esterase D enzyme. GM1142 and GM2718 contained quantitatively less activity than the others. These findings are consistent with the observation (FIG. 6C. c+d) that GM1142 and GM2718 have only a single copy of the esterase D gene.

Southern genomic blotting analysis showed that the esterase D gene was distributed over 20–40 kb in the human genome (FIG. 6B). The combined size of the DNA fragments with positive hybridization was 20–40 kb, indicating that there are large introns sequences in the ESD genome. This was subsequently confirmed by characterizing the complete genomic esterase D clone (FIG. 8).

The esterase D gene has been mapped to the chromosome 13q14.11 region by correlating loss of the esterase D enzyme activity with known deletions on chromosome 13 of various mutant cells. To determine the location of the EL22 clone, several human mutant cell lines containing well-characterized deletions for chromosome 13 were selected. These human mutants—namely human mutant fibroblast, GM1142, GM2718 and GM3887—were obtained from Human Genetic Mutant Cell Repository in Camden, N.J. DNA extracted from these mutant cells were subjected to Southern genomic blotting analysis by using the EL22 clone as probe. As shown in FIG. 6C, a Chinese hamster ovarian cell (CHO) human fibroblast hybrid cell line 34-2-3, containing two or three copies of chromosome 13, one copy of chromosome 12, and one copy of chromosome 6p in its tetraploid CHO genome, showed a hybridization pattern (lane b) indistinguishable from that of human peripheral lymphocyte DNA (lane a). The hybridization intensity observed in this cell line was between that observed in haploid cells, as described below, and that observed in diploid cells such as peripheral lymphocytes (lane a), suggesting that the esterase D gene is located in human chromosome 13. In contrast, DNA from CHO cells hybridized weakly with the EL22 clone and showed a different pattern from that of human DNA. Furthermore, DNA obtained from two mutant cell lines, GM1142 and GM2718, with visible deletions at 13q12-14 and 13q14-22, respectively, showed an identical hybridization pattern with about one-half the intensity of that found in lymphocytes (lanes c and d). This suggests that they contain the haploid esterase D gene, which is apparently not located at the deletion junction. However, this reduced intensity was not found in the mutant cell line GM 3887, which was deleted at 13q22-ter or in Y79 cells, which had no visible deletion in chromosome 13. To provide an internal control, the same blot was hybridized with the v-myc gene. With the exception of the 34-2-3 cell line, which did not contain the 13.5-kb c-myc gene, the rest of the DNA samples showed essentially identical hybridization intensity at the 13.5 kb c-myc gene, demonstrating that the quantitation was reliable. These results, therefore, indicate that the EL22 clone containing the esterase D gene is mapped to the chromosome 13q14 region.

Using the esterase D cDNA as probe, it was found that (i) the size of the esterase D mRNA is 1.3-1.4 kb; (ii) the gene is around 20-35 kb, indicating the presence of large introns scattered over this genome; and (iii) the esterase D gene is indeed located at 13 chromosome 13q14 region. Also, the deduced amino acid of the esterase D gene was unique when compared to 4000 other well-characterized proteins (FIG. 9).

The above obtained mapping data shows that the ESD gene is located at chromosome 13q14.11 region with no meiotic recombination observed with the RM gene. These findings indicate that both genes are in close proximity although the exact kilobase-pair distance between them is unknown. Normally, the maximal DNA content of a band, such as q14:11 does not exceed, on the average, 1000 kb. On the other hand, the distance between the RB gene and the ESD gene may be just a few kilobases. Based on the lack of esterase D activity in LA-RB 69 retinoblastoma cells, it was previously suggested that a submicroscopic deletion had occurred in the tumor cells resulting in the loss of both the RB and the esterase D genes. *Science*, 219:973–975 (1983). Deletion in the coding sequences of the esterase D gene in the tumor cells was not found in current experimentation. However, some abnormality, perhaps in the regulatory region, must have occurred to cause a substantial reduction in the expression of the esterase D gene and diminution of the enzyme activity. It is plausible to expect that this abnormality would be likely to interfere with the RB gene expression leading to tumorigenesis.

Since the esterase D gene is known to be located in close vicinity to the RB gene, it will be useful as the starting point for identifying the RB gene by chromosomal walking. DNA fragments isolated from this process can then be used as probes to examine qualitative or quantitative differences in mRNA from fetal retinal cells and retinoblastoma cells. Detection of such differences would provide evidence that somatic mutations occur in the RB gene of tumor cells. The DNA fragments corresponding to the defective mRNA are the best candidates for the RB gene. Moreover, the availability of mutant cells with known deletions in 13q13.1-14.11 and 13q14.11-q22, respectively, will enable determination of the correct direction of walking toward the RB gene.

The current invention has many aspects. It provides purified ESD; the method of purification of ESD; the preparation of specific polyclonal anti-esterase D antibodies; human ESD cDNA and its nucleotide sequence; a radioactive human ESD cDNA probe; chromosomal mapping localization and nucleotide sequence identification of the human ESD gene; and the ESD amino acid sequence and genomic clones of ESD gene.

The current invention has many utilities. The purified ESD may be used for preparation of specific polyclonal anti-esterase D antibody and for elucidation of the function of various esterases present in the body. The anti-esterase D antibodies are useful for detection of ESD by immunoprecipitation and for recognition by immunoscreening of the ESD cDNA clones. Expression libraries from human hepatoma and human placenta are useful for identification and cloning of ESD gene. The preparation of synthetic labeled oligomeric probes is useful for identification of the ESD gene nucleotide sequence. The complete nucleotide sequence of the ESD gene is useful for isolation and identification of the retinoblastoma and Wilson's disease genes by chromosomal walking and for their diagnosing.

The cloned ESD cDNA may be also used as the polymorphic marker to diagnose retinoblastomas and Wilson's disease through the method of restriction fragment length polymorphism. In addition, the polymorphic nature of the ESD protein may be useful as a method for detecting single point mutations. Only about 10% of informative polymorphism because of the presence of only three isoenzymes (ESD1-1, ESD2-1, and ESD2-2), the in the retinoblastoma family, the large size of the intron sequences in the esterase D genome, as defined by this invention, should provide sufficient possibilities for finding more variety of polymorphic markers. The distinct characteristics of the esterase D gene and its adjacent DNA fragments offer therefore highly specific and accurate diagnosis of hereditary diseases controlled by genes localized in close proximity of the esterase D gene.

DESCRIPTION OF THE FIGURES

FIG. 7 illustrates the esterase D cDNA-complete sequence.

FIG. 7A schematically depicts the sequence of FIG. 7;

FIG. 8 depicts the nucleotide and deduced amino acid sequences of EL22 cDNA.

FIG. 9 is the esterase D amino acid sequence.

DETAILED DESCRIPTION OF THE FIGURES

Figures 1A, 1B:
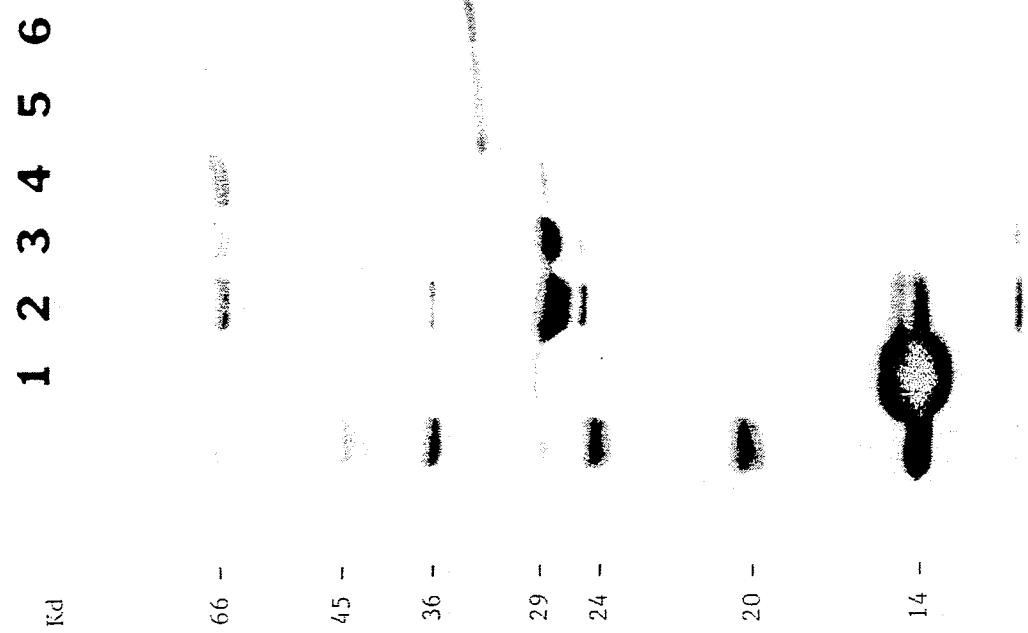
FIG. 1. is a photography of the agarose gel and NaDodSO$_4$/polyacrylamide gel electrophoresis used for monitoring of ESD.

FIG. 1(A) shows NaDodSO$_4$/PAGE of proteins following the sequential purification steps of esterase D. Lanes:
(1) erythrocyte lysate (25 μg);
(2) supernatant of chloroform/butanol extraction (10 μg);
(3) proteins not bound to MC-cellulose (5 μg);
(4) pooled fractions with enzyme activity after Phenyl-Sepharose column (2.5 μg);
(5) peak fractions of chromatofocusing column (1 μg); and
(6) peak fractions of hydroxypalatite column (1 μg).
Bovine serum albumin, ovalbumin, glyceraldehyde-3-phosphate dehydrogenase, carbonic anhydrase, trypsinogen, soybean trypsin inhibitor, and lactalbumin were used as molecular size markers.

FIG. 1(B) shows agarose gel electrophoresis to distinguish esterase D from other esterases. Lanes:
(1) supernatant of chloroform/butanol extraction;
(2) fraction not bound to CM-cellulose;
(3) fractions from the Phenyl-Sepharose column;
(4) fractions from the chromatofocusing column;
(5-7) fractions of esterase D after hydroxypalatite; and
(8-9) fractions of esterase X after hydroxypalatite.
Arrows indicate the migration of esterases D and X in this gel.

Figure 2A:
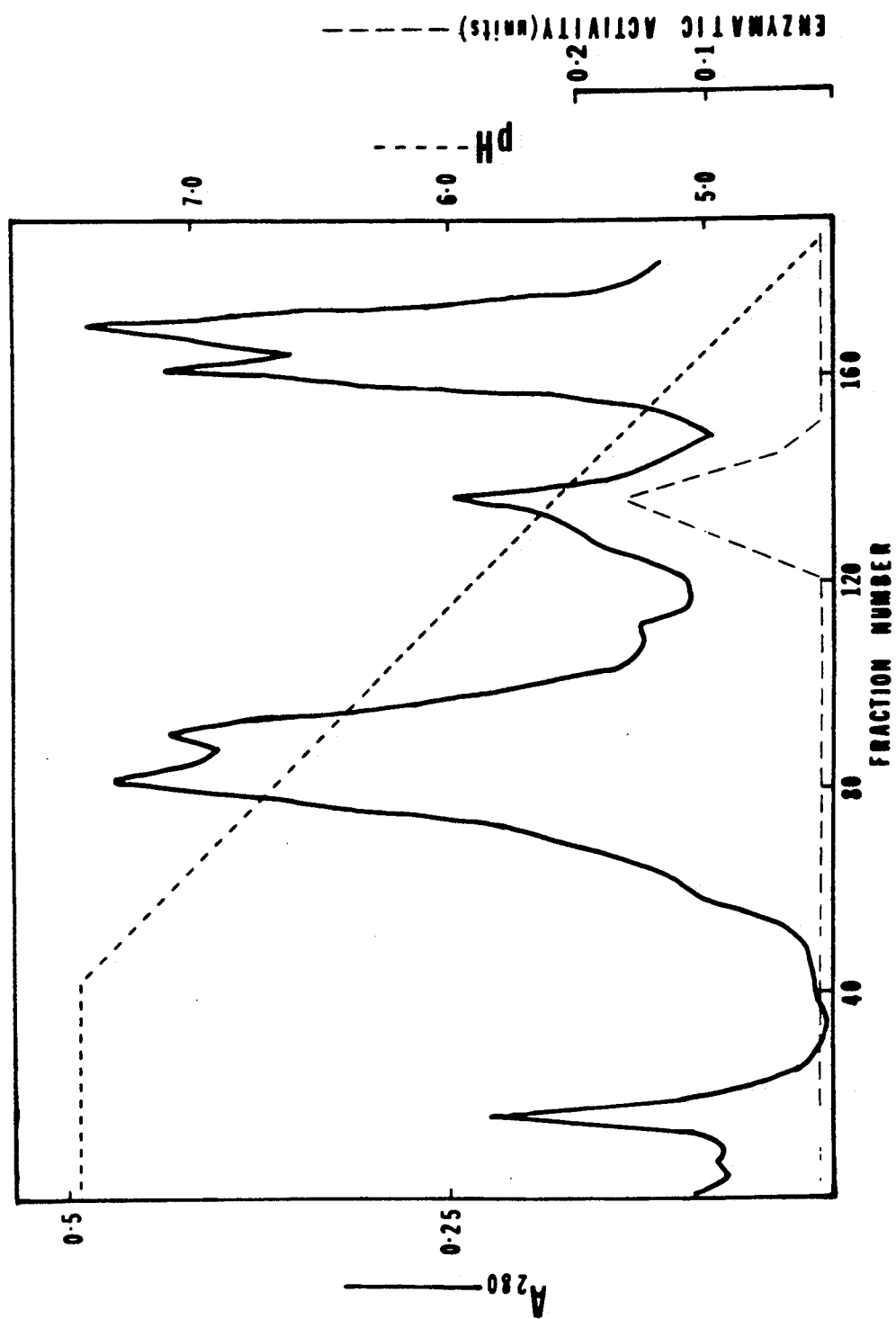
FIGS. 2A and 2B, are diagrams showing column chromatography profiles of ESD.
Figure 2B:
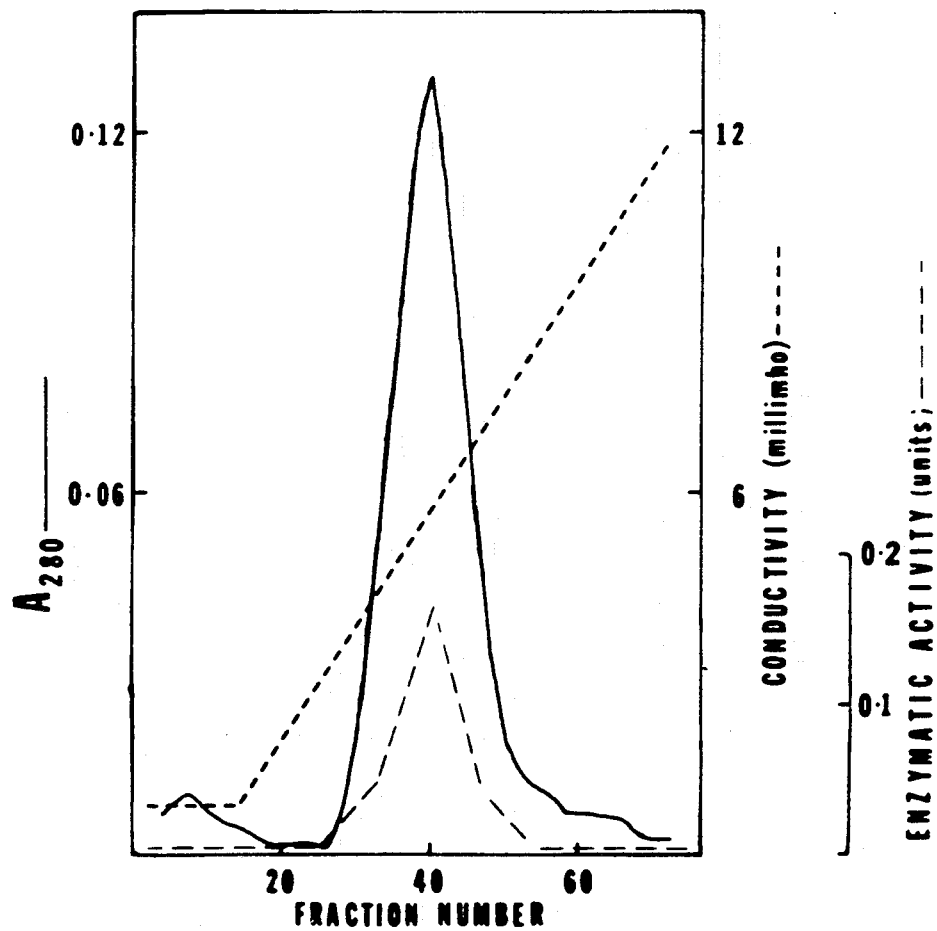

FIGS. 2A and 2B illustrate a column chromatography profile of esterase D.

As shown in FIG. 2A, fractions from the Phenyl-Sepharose column containing enzymatic activity were concentrated and chromatographed on a chromatofocusing column (1.0×62 cm) in 25 mM imidazole buffer (pH 7.4), fractions were eluted with polybuffer 74 (pH 4.0). 3.7 ml fractions were collected.

As shown in FIG. 2B, proteins with enzyme activity from fractions A of FIG. 2A separated on a hydroxypalatite column, equilibrated with 10 mM potassium phosphate buffer (pH 7.0) and eluted with a 0–0.4M ammonium sulfate gradient. 2 ml fractions were collected. The active enzyme peak was detected by spot test and quantitative assay as described in Example 1.

FIG. 3 shows specificity of rabbit polyclonal antibodies. Three sets of partially purified esterase D preparation were electrophoresed on a 12.5% slab gel. One set was stained with Coomassie blue (A). The rest was electroblotted to a nitrocellulose filter. One strip was incubated with rabbit polyclonal antibodies (B). Both strips were further incubated with $^{125}$I-labeled protein (A) and exposed on Kodak XAR-5 film.
Lanes:
(a) proteins after Phenyl-Sepharose;
(b) after chromatofocusing; and
(c) after hydroxypalatite, as described in FIG. 1.(D). Immunoprecitiation by rabbit polyclonal antibodies of esterase D labeled with [$^{35}$S]methionine from different cell lines of several mammalian species. The precipitated proteins were analyzed on a 12.5% polyacrylamide gel followed by fluorography.
Lanes:
(a) CHO cells (hamster);
(b) 3T6 cells (mouse);
(c) rat-2 cells (rat);
(d) COS cells (monkey); and
(e) U937 cells (human).

In addition to the esterase D protein of 33-34 kDa (marked with arrow), some unknown proteins were also coprecipitated.(E) Enzymatic activity with immunocomplex of immunized rabbit IgG and esterase D enzyme. An equal amount of esterase D enzyme (0.5 $\mu$g) was incubated with a series of different quantities of IgG (a) 24$\mu$; (b) 12 $\mu$g; (c) 6 $\mu$g; (d) 3 $\mu$g) and precipitated with protein A-Sepharose beads. After several cycles of washing, the Sepharose beads were spotted with 4-methylumbelliferyl acetate and photographed under UV light. The four controls were as follows: (e) normal rabbit IgG; (f) beads alone; (g) beads incubated with enzyme without the IgG; (h) 0.5 $\mu$g of esterase D enzyme.

As shown in FIG. 4, profile of CNBr-cleaved esterase D protein separated by reversed-phase HPLC (Brownlee RP 300)(A), and partial amino acid sequences of three CNBr-cleaved peptides and the corresponding sequences used to construct the synthetic oligonucleotide probe mixture (B).

As shown in FIG. 5, identification of positive esterase D clones from $\lambda$gt11 cDNA libraries. (A) Positive clones detected by autoradiography, EL22a and EL22b, were lysogenized in *E. coli* Y1090 and induced to express fusion proteins. Lysate samples of the parental BNN103 ($\lambda$gt11)(lane a), Y1090(EL22a)(lane b), and Y090(EL22b)(lane c), were analyzed on a 7.5% NaDodSO$_4$/polyacrylamide gel and stained with Coomassie brilliant blue. $\beta$-galactosidase(114 kDa) was clearly induced and expressed in BNN103($\lambda$gt11), but the expression of any fusion protein of EL22 was not apparent. Duplicate samples on the same polyacrylamide gel were electrotransferred onto a nitrocellulose filter. The filter was first preincubated with 3% nonfat dry milk in TBS (Tris-buffered saline; 0.17M NaCl/0.01M Tris-HCl, pH 7.5) for 1 hour and then incubated with rabbit IgG specific to esterase D in 1% gelatin for 12 hour. After washing with TBS, the filter was further incubated with $^{125}$I-labeled protein A for 2 hour. A fusion protein of 145 kDa was detected in the recombinant lysogen of EL22a and EL22b (lanes b' and c') but not in the parental strain (lane a).
(B) Hybridization of $^{32}$P-labeled 23-mer to EL22a (lane a) and EL22b (lane b). DNA from recombinants $\lambda$EL22a and EL22b were digested with EcoRI and electrophoresed through a 0.8% agarose gel. The digested DNA fragments were then transferred onto a nitrocellulose filter and hybridized with $^{32}$P-labeled 23-mer in 6$\times$SSC at 37° C. (1$\times$SSC=0.1 Mm NaCl/0.015M sodium citrate). A DNA fragment of 1.1 kb was detected under the washing condition of 3$\times$SSC at 37° C.

FIG. 6 is a blotting analysis of esterase D mRNA (A), genomic DNA (B), and the localization of the EL22 clone on human chromosome 13q14(C). The probe used in these experiments was $^{32}$P-labeled pUCEL22 DNA. (A) Poly(A)-selected mRNA of Y79 cells (lane a) and LA-N-5 cells (lane b) was used for RNA blotting analysis. These two cell lines were chosen because they contained a sufficient amount of esterase D protein immunoprecipitable by the rabbit anti-esterase D antibodies. The esterase D mRNA size of these two cell lines is $\approx$14.5 S. However, the apparent size of LA-N-5 mRNA appeared slightly larger than Y79, which was probably caused by partial degradation.
(B) High molecular weight genomic DNA from human peripheral blood lymphocyte (PBL) was digested with Pst I (lane a) and Sst I (lane b) and electrophoresed on a 0.8% agarose gel, followed by Southern blotting analysis. The combined size of the DNA fragments with positive hybridization was 20–40 kb, indicating that there are large intron sequences in the esterase D genome.
(C) DNA was extracted from: (i) PBL (normal peripheral blood lymphocytes (lane a); (ii) 34-2-3 (Chinese hamster-human hybrid cells containing human chromosomes 13, 12 and the short arm of 6 (lane b); (iii) GM1142 [$\Delta$13(q14:q22)](lane c); (iv) GM2718 [$\Delta$13(q12:q14)](lane d); (v) GM3887 [$\Delta$13(q22:qtr)](lane e); and (vi) Y79 (human retinoblastoma cells (lane f). After complete digestion with EcoRI, DNA fragments were analyzed by Southern genomic blotting. All the cells used here have esterase D enzyme; however, GM1142 and GM2718 contained quantitatively less activity than the others, which is consistent with the presence of a single copy of the esterase D gene as shown here. The same result has been replicated in three separate experiments.

The following examples further illustrate and present a preferred embodiment of the invention disclosed herein. The examples are not intended to limit the scope of the invention.

EXAMPLE 1

Purification of Human Esterase D

ESD was purified according to the following procedure.

Step 1. Outdated human erythrocytes were washed once in phosphate-buffered saline (PBS) with 1 mM EDTA. The erythrocyte lysate was submitted to quantitative and qualitative assays to determine the specific activity and the purity of ESD. A precooled (−20° C.) mixture of cloroform and butanol was added to the packed cells to concentrations of 6% and 15%, respectively according to method described in *Prep. Biochem.*, 6:147-152 (1976). The lysed cells were centrifuged at 23,000$\times$g for 20 min and >95% of the hemoglobin was pelleted at this step. Buffers used in the subsequent steps all contained 1 mM EDTA, 0.1% 2-mercaptoethanol, and 0.05 mM phenylmethylsulfonyl fluoride (PhMeSO$_2$F). The supernatant was then dialyzed overnight against several changes of 10 mM potassium phosphate buffer (pH 6.5).

The chloroform butanol extract was assayed to determine the specific activity and purity of ESD.

Step 2. Carboxymethylcellulose C52 equilibrated with 10 mM potassium phosphate buffer (pH 6.5) was added to the dialyzate to absorb the residual hemoglobin. The whole mixture was filtered through a sintered glass funnel and the filtrate was concentrated by precipitation with 90% saturated ammonium sulfate. The resulting mixture was assayed for ESD specific activity and purity.

Step 3. The protein precipitate was collected by centrifugation at 10,000×g for 10 min and resuspended in and dialyzed against cold distilled water until just clarified. The protein sample was loaded onto a phenyl-Sepharose CL-4B column (5×27.5 cm) equilibrated with 50 mM Tris-HCl buffer (pH 8.0) and 1M ammonium sulfate. The column was washed extensively with the same buffer and then eluted with a decreasing gradient of ammonium sulfate (1.0–0M) in 50 mM Tris-HCl buffer (pH 8.0). The fractions containing ESD were identified by spot test and the specific activity and purity was determined by qualitative and quantitative enzymatic tests (infra).

Step 4. The fractions from Step 3 showing the ESD activity from Step 3 were concentrated by precipitation with 90% saturated ammonium sulfate, resuspended in 25 mM imidazole buffer (pH 7.4), and then dialyzed against the same buffer. The sample was loaded onto a chromatofocusing column (1.0×62 cm) of Pharmacia Polybuffer Exchanger 94 gel, equilibrated with the same buffer and eluted with Polybuffer 74 (pH 4.0). The fractions containing ESD were identified by the spot test and the specific activity and purity were determined as above.

Step 5. The fractions with ESD activity from the chromatofocusing column were pooled, concentrated with ammonium sulfate, dialyzed against 10 mM potassium phosphate buffer at pH 7.0, and loaded onto a column of hydroxypalatite (1×9.5 cm) equilibrated with the same buffer. The enzyme was then eluted with a gradient of ammonium sulfate (0–0.4M) in the same buffer. The ESD fractions were identified and specific activity and purity determined as above.

Assays used for purification steps to determine the enzyme's specific activity, enzyme activity in column fractions, enzyme's phenotypic separation and purity were as follows:

Quantitative assay

ESD activity was determined essentially by method described in *Am. J. Hum. Genet.*, 30:14–18 (1975).

The reaction was started by adding the enzyme into 1 ml of reaction buffer containing 50 mM potassium phosphate, 1 mM EDTA (pH 6.0), with 0.1 mM 4-methylumbelliferyl acetate as substrate. The increase in absorbance at 340 nm was recorded. A unit of activity was defined as the amount of enzyme that hydrolyzed 1 μmol of substrate per min at 23° C. using 7.27 mM$^{-1}$ cm$^{-1}$ as the coefficient of absorption.

Spot test

A semiquantitative test was developed and used for rapid determination of the presence of enzyme activity in column fractions.

Briefly, 5 μl of 4-methylumbelliferyl acetate (20 μg/ml) in sodium acetate (pH 5.2) was spotted onto a piece of Saran Wrap over a UV transilluminator, 5 μl of enzyme samples from each column fraction was added and the presence of fluorescence was observed. The intensity of fluorescence emitted corresponded with the enzyme activity.

Qualitative assay

Electrophoresis in 1% agarose gel was performed essentially as described in *Humangenetik*, 28:75–78 (1975), with slight modifications outlined hereunder.

The agarose gel buffer was a 1:5 dilution of running buffer that contained 62 mM tris, 15.5 mM citric acid, 18 mM boric acid, and 1.65 mM lithium hydroxide (pH 7.5). Electrophoresis was performed at 4° C. for 90 min at 20V/cm. The gel was stained in 50 ml of 50 mM sodium acetate (pH 5.2) containing 1.0 ml of 4-methylumbelliferyl acetate (1 mg/ml in acetone) for 5 minutes and then photographed under UV light.

Purity of esterase D was monitored by NaDodSO$_4$/-polyacrylamide gel electrophoresis according to the procedures described in *Nature*, 227:680–685 (1970). Proteins were stained with either Coomassie brilliant blue or silver. Protein was quantitated by the method of Lowry *J. Biol. Chem.*, 193:265–275 (1951), with bovine serum albumin as the standard.

The purification scheme for ESD from human erythrocytes is summarized in Table 1. Each purification step of ESD was monitored as described by agarose gel and NaDodSO$_4$/polyacrylamide gel electrophoresis, by quantitative assay and by spot test when appropriate (FIG. 1).

Two steps, chloroform/butanol extraction and carboxymethyl-cellulose absorption, were necessary to remove all hemoglobin from the preparation. The remaining proteins were separated by Phenyl-Sepharose chromatography based on their hydrophobic nature. Peak activity of ESD was eluted in the range of 0.5M ammonium sulfate when an ammonium sulfate gradient (1–0M) was used (FIG. 1A, lane 4).

The spot test was used to quickly detect fractions containing esterase activity. The positive fractions were further subjected to agarose gel electrophoresis. Two forms of esterases with different mobilities were found (FIG. 1B). Further purification by chromatofocusing chromatography separated the two activities from each other (FIG. 2A). The faster migrating form has a molecular mass of 30 kDa in NaDodSO$_4$/PAGE. This previously unknown esterase was designated esterase X. The slower migrating form with a molecular mass of 34 kDa was ESD, which was confirmed by electrophoresis in a starch gel.

To remove minor contaminating proteins in the ESD pool, samples were further subjected to hydroxypalatite chromatography and eluted with a gradient of 0–0.4M ammonium sulfate (FIG. 2B). ESD eluted as a single peak and appeared to be homogeneous as judged by NaDodSO$_4$/PAGE (FIG. 1, lane 6). The purity of this preparation was further confirmed by sequency analysis. Using the present procedures, we achieved a 10,653-fold purification of ESD with 13% recovery. The total ESD protein in erythrocytes is ≈0.01%.

Biochemical Properties of the Purified Enzyme

1. Enzyme kinetics

To further characterize esterase D, we measured the K$_m$ of this purified ESD enzyme. The Km of ESD was determined to be 10×10$^{-6}$M by Lineweaver-Burk plots using 4-methylumbelliferyl acetate as the substrate. In contrast, the Km was 1.7 mM if naphthal acetate was used as the substrate. This 100- to 200-fold difference in substrate affinity was consistent with the original observation of Hopkinson et al., described in *Am. Hum. Genet.*, 37:119–137 (1973), demonstrating that ESD is rather specific for umbelliferyl acetate esters.

2. Enzyme inhibitors

Several chemicals such as mercuric chloride, p-chloromercuribenzoate, sodium fluoride, and PhMeSO$_2$F as well as specific antibodies were used to test for interference with the enzymatic activity of purified ESD (see Table 2). The enzymatic activity was inhibited completely by HgCl$_2$ and pcmb at very low concentrations, suggesting that an SH group is essential to the enzymatic reaction. However, only at high concentrations could NaF and PhMeSO$_2$F interfere with the enzyme activity. The prepared antibodies prepared did not affect the enzymatic activity even at high molar ratios of antibody to enzyme.

EXAMPLE 2

Preparation of Antibodies Against Esterase D

Polyclonal antibodies

New Zealand Red rabbits were initially injected with 10 μg of purified ESD protein mixed with complete Freund's adjuvant and then they were given booster injections of 10 μg of ESD protein in incomplete Freund's adjuvant for several months until high titers of antibody were detected by immunoblotting analysis according to *Proc. Natl. Acad. Sci.*, 76:4350–4354 (1979). When the antibody titer was sufficiently high to precipitate the ESD, the rabbits were bled and the blood was collected into plastic container and clotted. The serum was obtained by centrifugation at 1000 g for 10 minutes. Rabbit anti-esterase D immunoglobulin G (IgG) was purified by passing the antisera through the protein A-Sepharose column eluted with 0.1M glycine-HCl buffer at pH 2.3. The eluate was neutralized and passed though the esterase D column and eluted with the same buffer. The antibody was further absorbed with boiled *E. coli* strain Y1090 to remove any nonspecific binding. Antibody prepared through the above steps was serially diluted and the dilution sufficient to detect 1 ng of purified ESD protein spotted onto nitrocellulose filters was routinely used for screening cDNA libraries.

Immunoprecipitation

A standard protocol was followed as described in *J. Virol.*, 38:1064–1076 (1981).

Figures 3A, 3B:
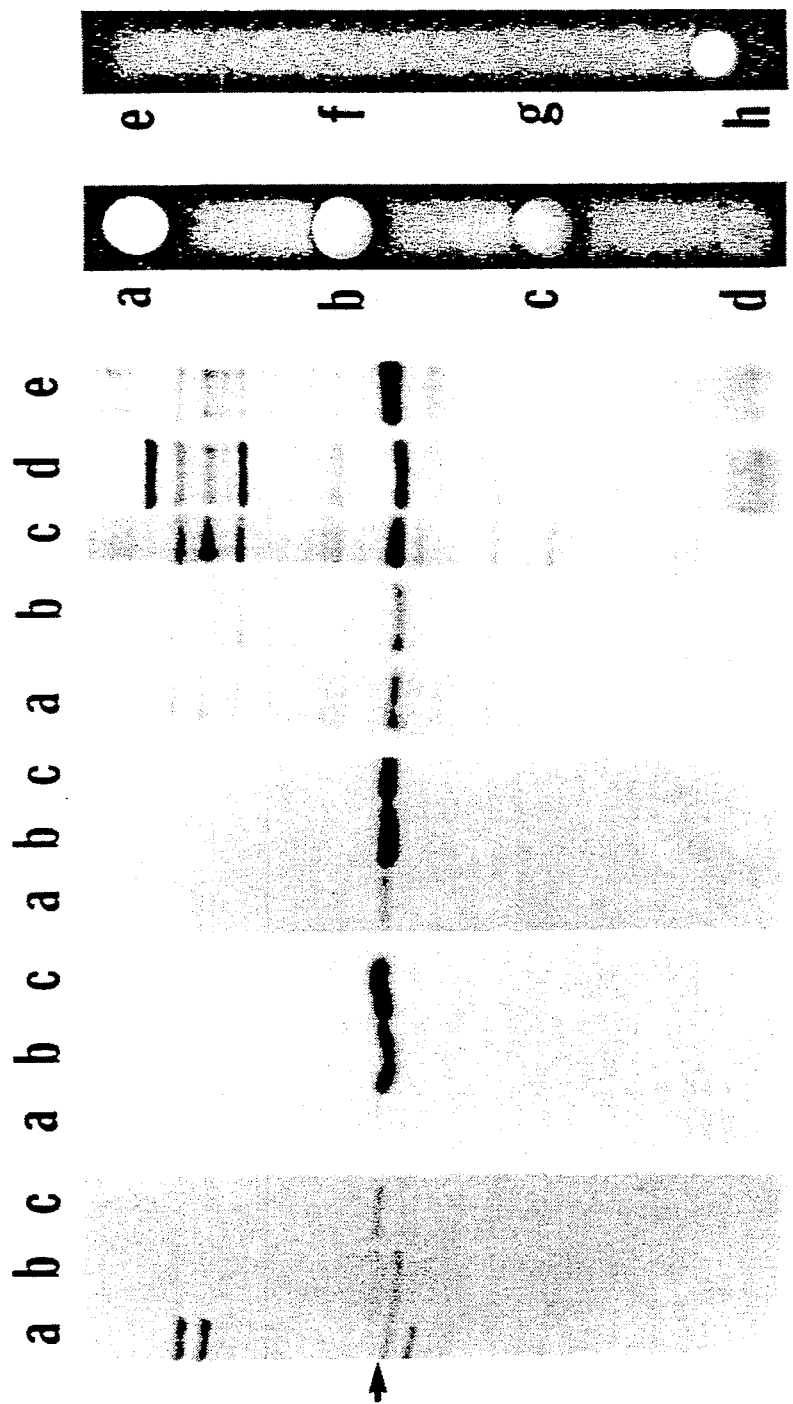
FIG. 3 is a chromatogram showing specificity of rabbit polyclonal antibodies.

Rabbit anti-esterase D IgG purified by protein A-Sepharose column chromatography and by ESD affinity column chromatography according to Example 1 was used in subsequent experiments. The IgG recognized the denatured esterase D protein in immunoblotting (FIG. 3B) as well as the native protein following immunoprecipitation (FIG. 3D). The immunocomplex of this IgG and the ESD enzyme remained active in hydrolysis of 4-methylumbelliferyl acetate, which further demonstrated the specificity of the IgG (FIG. 3E).

EXAMPLE 3

Determination of Amino Acid Sequence of Esterase D Protein

Purified human ESD protein prepared according to procedure described in Example 1, was treated with cyanogen bromide and the product was purified by reversed-phase HPLC (Brownlee RP 300). After the eluted polypeptides were dried, their amino acid sequences were determined by solid-phase Edman degradation with HPLC analysis of the phenylthiohydanton derivative as described in *Microcharacterization of Polypeptides: A Practical Manual*, Ed. J. E. Shively, Humana, Clifton, N.J. (1985).

Figures 4A, 4B:
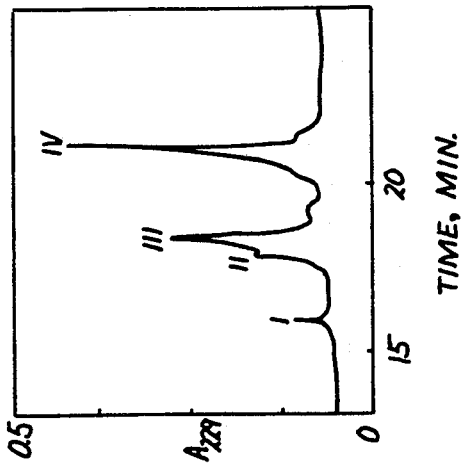
FIG. 4 is a diagram, illustrating profile of CNBr-cleaved esterase D protein (A) and partial amino acid sequences of three CNBr-cleaved peptides and the corresponding oligonucleotide sequences (B).

The purified ESD protein was characterized by sequence analysis starting from the NH$_2$ terminus by Edman degradation. However, no amino acid residue was obtained, suggesting that the N terminus was blocked. Further amino acid composition analysis of the protein showed four or five methionine residues. When the ESD protein was cleaved by cyanogen bromide, it cleaved into four resultant peptides, sequences of three of which are shown in FIG. 4B. The peptides profile of the cleaved ESD protein, obtained by purification and separation of HPLC, is shown in FIG. 4A.

Amino acid sequence from peptide I could not be obtained suggesting that it was located at the blocked N-terminus of the ESD protein.

The amino acid analysis of the remaining three peptides, namely peptides II, III and IV, has shown the methionine residue of:

13 amino acids for peptide II:
Met-Tyr-Ser-Tyr-Val-Thr-Glu-Glu-Leu-Pro-Glu-Leu-Ile-Asn;

13 for peptide III:
Met-Lys-Phe-Ala-Val-Tyr-Leu-Pro-Pro-Lys-Ala-Glu-Thr-Gly;

14 amino acids for peptide IV:
Met-Gly-Gly-His-Gly-Ala-Leu-Ile-Cys-Ala-Leu-Lys-Asn-Pro-Gly.

Each of the above peptide sequences, or the portion thereof, was used for construction of synthetic oligonucleotide probes according to Example 5.

EXAMPLE 4

Construction of Synthetic Oligonucleotide Probes

Mixed oligonucleotide probes were synthesized on a synthesizer using phosphotriester chemistry, (Dept. of Chemistry, University of California, San Diego). Three sets of oligonucleotide mixtures corresponding to the possible coding sequences of each peptide were constructed. The oligonucleotide mixtures were purified by gel electrophoresis on 20% polyacrylamide/8M urea gels and subsequently labeled at the 5' end with [γ$^{32}$P]ATP by using T4 polynucleotide kinase as described in *Molecular Cloning, A Laboratory Manual*, (Cold Spring Harbor Laboratory, Cold Springs Harbor, N.Y.).

The portions of three polypeptide amino acid sequences were used in constructing the oligonucleotide probes.

From peptide II amino acid sequence:
Met-Tyr-Ser-Tyr-Val-Thr-Glu-Glu-Leu;
was translated into nucleotide sequence:

$$5'\ \text{ATG}-\text{TA}_\text{T}^\text{C}-\text{TC}_\text{C}^\text{T}-\text{TA}_\text{T}^\text{C}-\text{GTN}-\text{ACN}-\text{GA}_\text{A}^\text{G}-\text{GA}_\text{A}^\text{G}-\text{CT}\ 3';$$

which in turn was chemically synthesized into 26-mer probe;

$$5'\ \text{AG}-_\text{T}^\text{C}\text{TC}-_\text{T}^\text{C}\text{TC}-\text{NGT}-\text{NAC}-_\text{A}^\text{G}\text{TA}-_\text{A}^\text{G}\text{GA}-_\text{A}^\text{G}\text{TA}-\text{CAT}\ 3'.$$

From peptide III amino acid sequence:
Met-Lys-Phe-Ala-Val-Tyr;
was translated into nucleotide sequence:

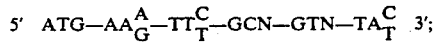

from which the oligonucleotide 18-mer probe of the following sequence was chemically synthesized:

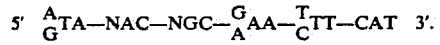

From peptide IV amino acid sequence portion:
Ile-Lys-Ala-Leu-Lys-Asn-Pro-Gly;
was translated to the nucleotide sequence;

from which the oligonucleotide 23-mer probe of the following sequence was chemically synthesized;

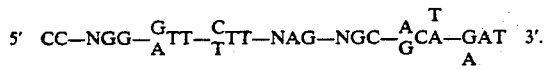

Under stringent hybridization conditions both 26- and 18-mer probes significantly cross-hybridized with λ vector of E. coli DNA. Therefore, only 23-mer probe was used in subsequent screening of appropriate ESD clones.

EXAMPLE 5

Antibody Screening of the λgt11 cDNA Library

Antibodies

Rabbit anti-esterase D antibodies were prepared against purified homogenous ESD enzyme as described in Example 2. The IgG fraction of this antibody was further purified by protein A Sepharose column chromatography and absorbed with boiled Escherichia coli strain Y1090 to remove any nonspecific binding. Optimum antibody concentrations and binding were determined by dot analysis with purified ESD protein.

cDNA Libraries

Two λgt11 cDNA libraries constructed using human hepatoma mRNA according to procedure described in DNA, 3:437-447 (1984) and human placenta mRNA according to procedure in J. Biol. Chem., 262:3112-3115 (1986), respectively, were plated on E. coli strain Y1090 and screened according to procedure described in Proc. Natl. Acad. Sci., 80:1194-1198 (1983).

In detailed procedure, 30 ml of fresh overnight grown bacteria Y1090 were pelleted and resuspended in 12 ml LB medium. $1 \times 10^6$ phages from human placenta or liver cDNA library were inoculated and incubated with the bacteria for 15 minutes in a 37° C. shaker and the mixture was then aliquoted and plated out on twelve 160 mm LB plates. The plates were incubated at 42° C. until plaque reached a size of 1 mm. This usually took 4 hours.

Each plate was covered with a nitrocellulose filter (Millipore Co.) that has been soaked in 10 mM isopropyl β-D-thiogalactoside (IpTG). These filters should be thoroughly dried before placing them on the plate. Filters were numbered with a ball point pen. Plates were incubated with filters at 37° C. overnight. The position of the filters was marked on the plate by piercing it with a needle containing India ink. The filter was transferred to a Whatman paper and 1 ng of purified esterase D (1 ng/μl) was dotted to the edge of the filter as a positive control. The phage plates were stored at 4° C. and a series of steps including blocking, incubation with antibody, washing, incubation with iodinated $^{125}I$ protein A and washing were performed on the nitrocellulose filters as follows:

The filter was placed in a crystal dish containing TBS+3% milk and shaken gently for 2 hour at room temperature. It was rinsed twice with TBS+1% gelatin. Then the filter was transferred to 80 ml of antibody prepared as described in Example 2 and incubated for 12 hours. Antibody was removed and the filter was washed with TBS+1% gelatin for 15 minutes, TBS+0.05% NP-40 for 10 minutes and TBS+1% gelatin for 10 minutes. The filter was then transferred to TBS+1% gelatin containing $1\times 10^6$ cpm of iodinated protein A, incubated for 4 hours and then washed with TBS+0.05% NP-40 for 20 minutes at room temperature three times. These filters were dried and exposed to XAR-5 film overnight.

The filter was used to locate the region on the phage plate corresponding to any positive signals on the X-ray film. A sterile pasteur pipet was used to remove the agar plug containing the area of the positive signal and to transfer it to 1 ml of SM buffer. The phage was eluted at 4° C. overnight. The screening procedure was repeated with dilution of the SM buffer phage stock until well separated plaques were obtained. The single plaque was then grown up in big scale for detail characterization.

From these two libraries, four positive clones were obtained. Two clones were very small with only about 150-200 base pairs inserts. The other two inserts were much larger, with identical 1.1 kilobase inserts. These two clones, called EL22a and EL22b, were induced to express β-galactosidase fusion protein. The result of this process is illustrated in FIG. 5.

Positive EL22a and EL22b clones from λgt11 cDNA libraries which were detected by autoradiography, were lysogenized in E. coli Y1090 and induced to express fusion protein as described above. Lysates of the control BNN103 λgt11 (FIG. 6, lane a), Y1090 EL22a (FIG. 6, lane b) and Y1090 EL22b (FIG. 6, lane c) were analysed by using a 7.5% sodium dodecyl sulfate/-polyacrylamide gel and stained with Coomassie brilliant blue. β-galactosidase which is known to be 114 kDa, was present, i.e. induced and expressed in the control λgt11 (FIG. 6, lane a) but the expression of EL22 fusion protein was not detectable.

Therefore, the duplicate samples on the same polyacrylamide gel were electrotransferred into a nitrocelluose filter which was first preincubated with 3% non-fat dry milk in Tris-buffered saline (0.17MNaCl/0.01M Tris HCl, ph 7.5) for 1 hour and then incubated with rabbit anti-esterase D IgG in 1% gelatin for 12 hours. After washing with Tris buffer, the filter was incubated with $^{125}I$ labeled protein A for 2 hours. In the recombinant lysogen of EL22a and EL22b, a fusion protein of 145 kDa was detected (FIG. 6, lanes b and c), which protein was not detected in the control BNN103 strain (FIG. 6, lane a). The protein of β-galactosidase alone is only 114 kDa, therefore, the remaining fragment of approximately ≈31 kDa was presumed to be encoded by the insert of the certain portion of EL22. The ≈31k$^D$a insert contained >90% of the sequence for complete ESD protein, which is known to have a molecular mass of 34k$^D$a.

EXAMPLE 6

ESD Gene Identification and DNA Sequence

To test whether the EL22 clone contains the ESD gene and if so, what the nucleotide sequence of the gene is, the $^{32}$p labeled 23-mer oligonucleotide probe to EL22a and EL22b obtained in Example 4, was used in Southern blotting analysis.

Human mutant fibroblasts, GM1142, GM2718, and GM3887, were obtained form the Human Genetic Mutant Cell Repository (Camden, N.J.) and characterized as described in *Am. J. Hum. Genet.*, 36:10–24 (1984). Human retinoblastoma cell line Y79, neuroblastoma cell line LA-N-5, and Chinese hamster-human hybrid cell line 34-Z-3 were provided as described in *Nature*, 309:458–460 (1984) and *Cytogenet. Cell Genet.*, 28:116–120 (1980). All these cells were grown in Dulbecco's modified Eagle's medium (GIBCO) supplemented with 10% fetal calf serum.

Genomic DNA was extracted from these cells as described in *Molecular Cloning: A Laboratory Manual,* Cold Spring Harbor Laboratory, Cold Springs, N.Y. (1982).

Human genomic DNA (10 μg) from different cells was digested with restriction endonuclease EcoRI and subjected to electrophoresis. Genomic blots were hybridized with 32p-labeled EL22 cDNA clone.

Figures 5A, 5B:
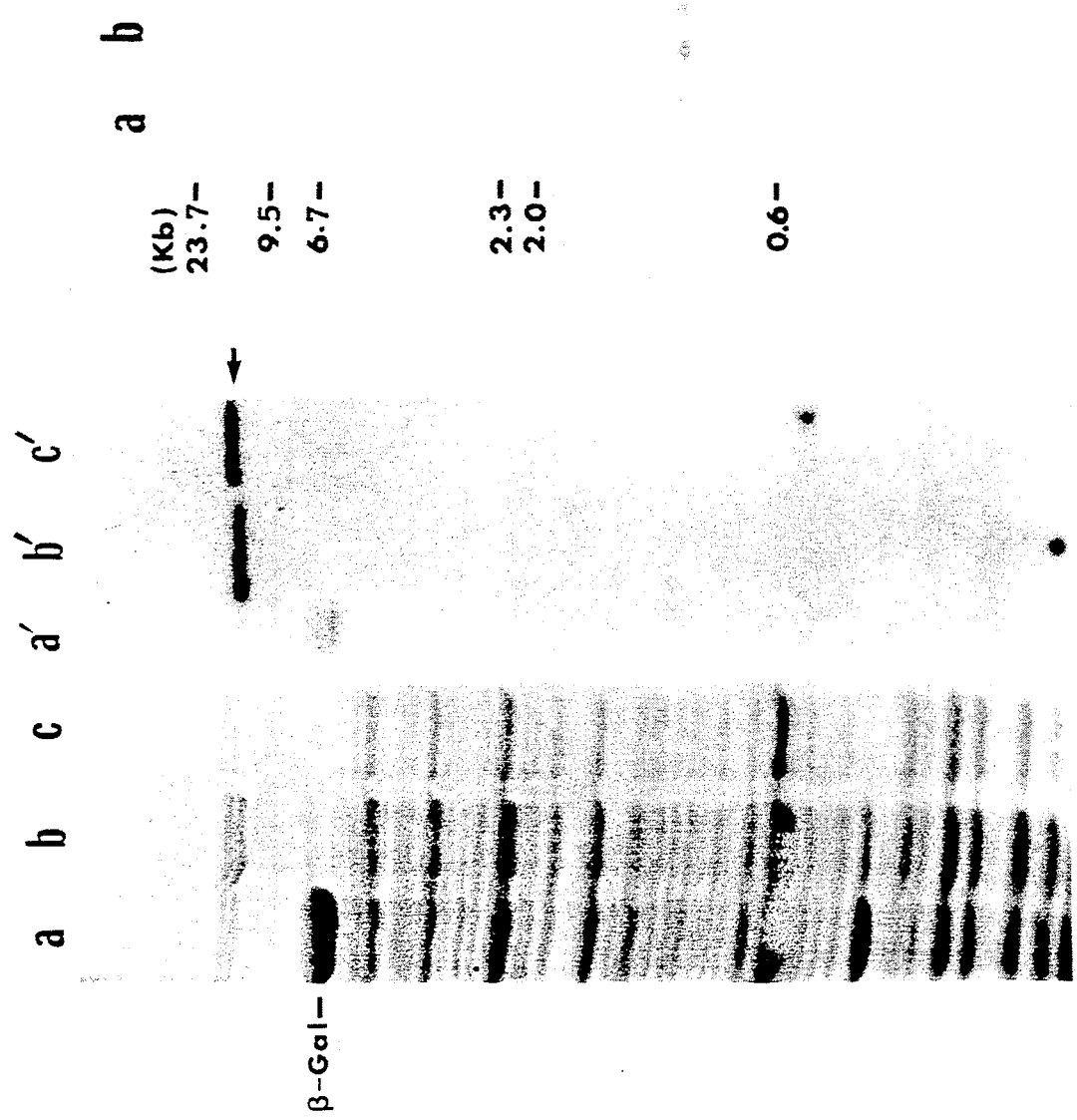
FIG. 5 is a chromatogram illustrating identification of positive ESD clones from λgt11 cDNA libraries.

As shown in FIG. 5B, one 1.1 kb EcoRI digested DNA fragment hybridized specifically to the $^{32}$P-labeled 23-mer probe when DNA from recombinants λEL22a and λEL22b were digested with EcoRI and electrophoresed through a 0.8% agarose gel. The digested DNA fragments were then transferred onto a nitrocellulose filter and hybridized with $^{32}$P-labeled 23-mer in 6×SSC at 37° C. (1×SSC=0.15MNaCL/0.015M sodium citrate). A DNA fragment of 1.1 kb was detected under the washing conditions of 3×SSC at 37° C.

DNA fragment/23-mer oligonucleotide probe hybridization, in addition to the immunological results, also proved that the EL22 clone contains the ESD gene.

DNA Sequencing

The EL22 clone was further characterized by DNA sequence analysis.

The λEL22 clone obtained in Example 5, containing a 1.1 kb (i.e. 1100 base pair) EcoRI insert, was subcloned into M13 phage mpll at the EcoRI site. The single-stranded DNAs of two recombinants with opposite orientation were isolated and used to construct 3' deletion mutants as described in *Plasmid* 13:31–40 (1985). Five mutants with different lengths of insert from each parental clone were sequenced by using the dideoxynucleotide chain-termination method described in *Proc. Natl. Acad. Sci.*, 74:5463–5467 (1977).

Approximately 95% of the double-stranded DNA was sequenced as shown in FIG. 7. A long open reading frame encoding a protein of 31kD was found. The three stretches of amino acid sequences, i.e. peptides II, III and IV, obtained in Example 4, from CNBr-cleaved ESD protein were identically matched to the deduced protein sequence, as can be seen in FIG. 7. (Peptides II, III and IV in the sequence are underlined).

This data prove that the EL22 clone is the esterase D cDNA. Based on the amino acid sequences and on the size of the ESD protein, it is evident that some 20–30 amino acid close to or attached to NH$_2$ terminus of ESD are not found in the EL22 clone.

Using the sequencing method as described above the complete sequence of esterase D cDNA was determined. (FIG. 8).

EXAMPLE 7

Size of Esterase D mRNA and of Esterase D Genome

RNA blotting analysis was performed to determine the mRNA size of the esterase D gene by using poly(A)-selected mRNA from two cell lines, Y79 and LA-N-5, as described in *Nature*, 309:458–460 (1984). Human retinoblastoma cell line Y79, neuroblastoma cell line LA-N-5, were provided as described (Ibid), The cells were grown in Dulbecco's modified Eagle s medium (GIBCO) supplemented with 10% fetal calf serum. Genomic DNA was extracted from these cells. Cellular messenger RNA was prepared by the guanidine isothiocyanate/cesium chloride method and enriched by oligo(dT)-Sepharose column chromatography according to the method described in *Molecular Cloning: A Laboratory Manual* (Supra).

RNA Blot Analysis

Poly(A)-enriched mRNA was prepared and electrophoresed on 1.2% agarose containing formaldehyde and transferred to a nitrocellulose filter using a method described in Example 4. The RNA blot was hybridized with the $^{32}$P-labeled EL22 cDNA clone.

Figures 6A, 6B:
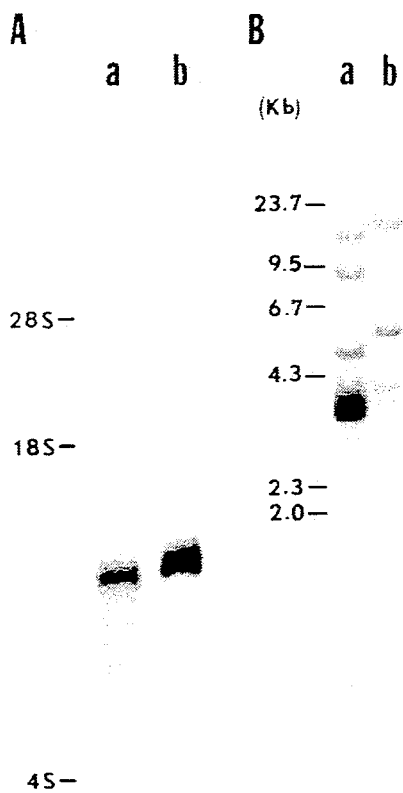
FIG. 6 is a chromatogram showing a blotting analysis of esterase D mRNA(A), genomic DNA(B), as well as the localization of the EL22 clone on human chromosome 13q14(C).

A mRNA of ≈14.5S(0.13–1.4 kb) was hybridized with the $^{32}$P-labeled EL22 clone (FIG. 6A). Southern genomic blotting analysis described in Example 6, using the same $^{32}$P-23-mer probe showed that the esterase D gene was distributed over 20–40 kb pairs in the human genome (FIG. 6B). This analysis indicates the presence of large introns within this gene FIG. 8.

EXAMPLE 8

Chromosome Mapping

The esterase D gene has been mapped to the chromosome 13q14.11 region by correlating loss of the esterase D enzyme activity with known deletions on chromosome 13 of various mutant cells.

To determine the location of the EL22 clone, several human mutant cell lines containing well-characterized deletions for chromosome 13 were selected. These human mutants—namely human mutant fibroblast, GM1142, GM2718 and GM3887—were obtained from Human Genetic Mutant Cell Repository in Camden, N.J.

Figure 6C:
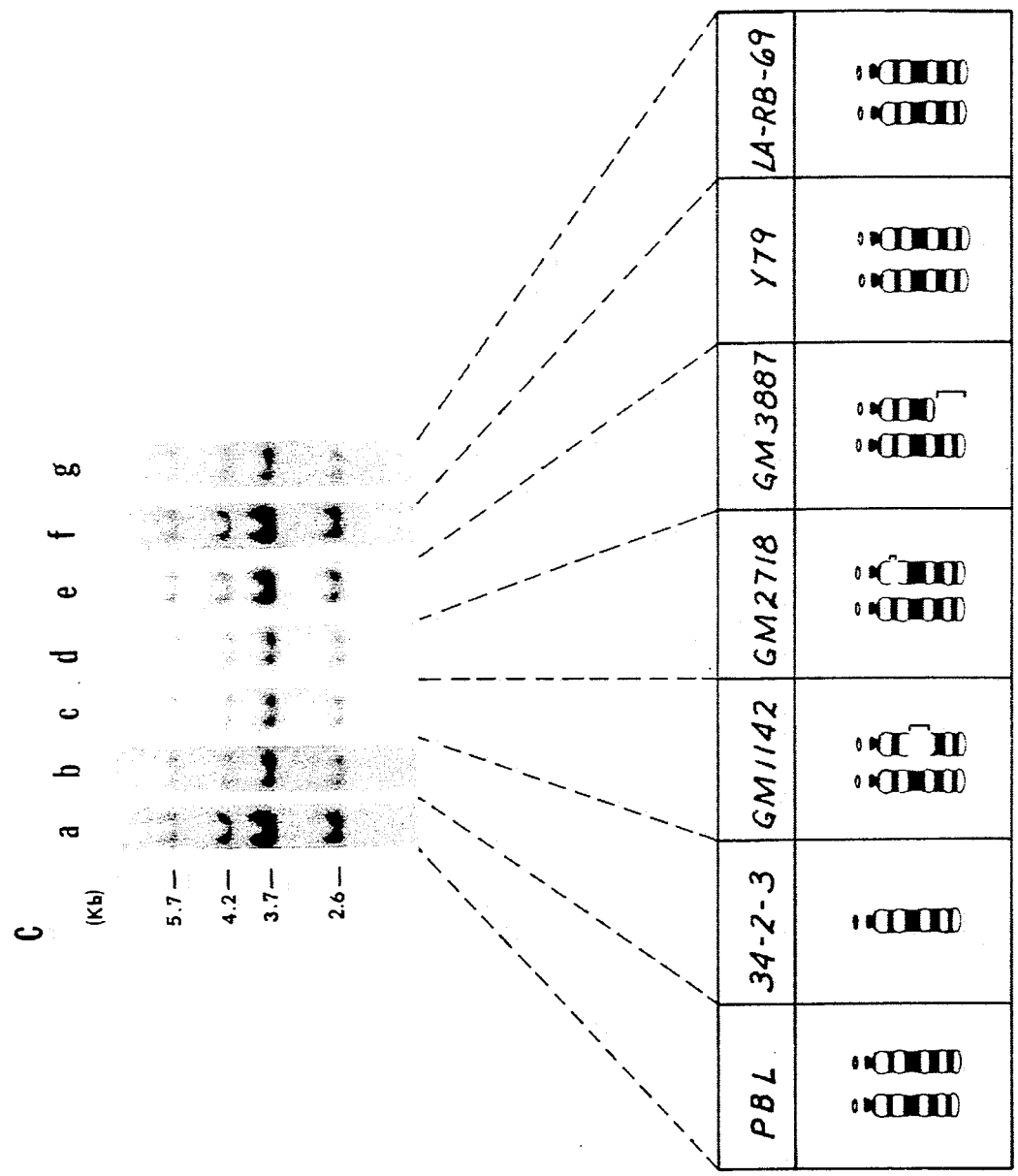

DNA extracted from these mutant cells were subjected to Southern genomic blotting analysis by using the EL22 clone as probe. As shown in FIG. 6C, a Chinese hamster ovarian cell (CHO) human fibroblast hybrid cell line 34-2-3, containing two or three copies of chromosome 13, one copy of chromosome 12, and one copy of chromosome 6p in its tetraploid CHO genome, showed a hybridization pattern (lane b) indistinguishable from that of human peripheral lymphocyte DNA (lane a). The hybridization intensity observed in this cell line was between that observed in haploid cells, as described below, and that observed in diploid cells such as peripheral lymphocytes (lane a), suggesting that the esterase D gene is located in human chromosome 13. In contrast, DNA from CHO cells hybridized weakly with the EL22 clone and showed a different pattern from that of human DNA. Furthermore, DNA obtained from two mutant cell lines, GM1142 and GM2718, with visible deletions at 13q12-14 and 13q14-22, respectively, showed an identical hybridization pattern with about one-half the intensity of that found in lymphocytes (lanes c and d). This suggests that they contain the haploid esterase D gene, which is apparently not located at the deletion junction. However, this reduced intensity was not found in the mutant cell line GM 3887, which was deleted at 13q22-ter or in Y79 cells, which had no visible deletion in chromosome 13. To provide an internal control, the same blot was hybridized with the v-myc gene. With the exception of the 34-2-3 cell line, which did not contain the 13.5-kb c-myc gene, the rest of the DNA samples showed essentially identical hybridization intensity at the 13.5-kb c-myc gene, demonstrating that the quantitation was reliable. These results, therefore, indicate that the EL22 clone containing the esterase D gene is mapped to the chromosome 13q14 region.

What is claimed is:

1. A DNA sequence selected from the group consisting of a cDNA encoding human esterase D and, fragments thereof which encode proteins having the enzymatic activity of esterase D.

2. The cDNA of claim 1 wherein the cDNA sequence is mapped to chromosome 13 region 13q14, sub-band 11.

3. The DNA sequence of claim 1 which is encoded by the EL-22 clone or a fragment thereof which encoded a protein having the enzymatic activity of esterase D.

4. The DNA sequence of claim 1 which is encoded by the esterase D cDNA clone EL-22A derived from human hepatoma.

5. The DNA sequence of claim 1 which is encoded by the esterase D cDNA clone EL22B derived from human placenta.

6. A method of cloning esterase D cDNA comprising:
    (a) constructing a λgt11 library from human tissue mRNA;
    (b) screening said library with esterase D antibody;
    (c) isolating positive phages; and
    (d) repeating steps (a) through (c) until a pure population of esterase D cDNA is obtained.

7. An isolated and purified DNA fragment having the following nucleotide sequence:

| | | | | | | | | | | | | | | | | | | | |
|---|---|---|---|---|---|---|---|---|---|---|---|---|---|---|---|---|---|---|---|
| 5' | | | | | | | | | | | | | | | | | | | |
| 1 | GAA | TTC | CGG | CGG | CCA | TCT | TGA | GCC | CCG | CCT | TTT | ACT | TCG | GCC | CGC | TTC | TTC | TGG | TCA | 60 |
| 61 | CTC | CGC | CTC | CGT | ATC | GCC | TAC | CAT | TTG | GTG | CAA | GCA | AAA | AGC | AAT | CAG | CAA | TTG | GAC | 120 |
| 121 | AGG | AAA | AGA | ATG | AGT | AAG | CAG | ATT | TCC | AGA | ATG | AAG | GGT | GGA | GGA | TTA | CAA | CCA | AAA | 180 |
| 181 | GTT | TTT | GAC | ACA | GGA | GTT | GCA | GAA | TGC | AAA | ATG | TGG | TGG | CTT | CCA | GTC | TAC | TTA | ACA | 240 |
| 241 | CCA | GAG | GCA | AAT | ATA | TCA | AAG | TAT | CCT | GCT | CTC | TCT | GCT | GCT | AAA | GGT | AAT | ACT | GGT | 300 |
| 301 | GTC | CAA | CAA | ATT | GAT | ACT | TCA | CCA | AGC | AGC | TTT | TCA | CAA | CAA | CAA | GAA | CTT | AGC | AAC | 360 |
| 361 | GAC | TTT | GCT | TAC | ACT | GGC | TTT | AGC | GTT | GTC | GAG | GTC | TTT | AAA | CTC | GAA | CAA | CTG | AGT | 420 |
| 421 | TAC | AGA | TCT | CAA | TAT | ATG | TCT | ACA | TTT | CAC | CTT | TAC | AAT | GCC | GGA | AAA | TTT | GAG | GAT | 480 |
| 481 | CGT | GCT | TGG | CCC | GTT | GGA | TTG | GGA | AAA | GCC | CTT | ATG | CAA | CTC | AAA | GCT | ATT | TAG | GGT | 540 |
| 541 | CCT | GCA | TGT | CTG | AAG | ATT | GCT | TAT | CAA | CTT | GGC | TTC | CAG | CAA | ACC | GAC | CGT | TTG | GAT | 600 |
| 601 | TGT | AGG | CTA | CTC | CAG | CAT | ATA | ATC | CCC | GGA | GCA | TCA | GGT | ATC | CTG | GGA | CAG | CTC | CAT | 660 |
| 661 | AAA | CCT | GTA | TTC | AGC | AAG | GAT | GCT | TAT | AAA | ACC | CAG | ATT | GTT | TCA | CTT | TTA | CAA | CAT | 720 |
| 721 | ATA | AAC | CTA | TTC | ATT | ATA | CAT | AGC | CCC | AGC | TGG | AAT | AGA | ATC | AAC | GAT | CTC | GAG | AAA | 780 |
| 781 | TAT | AAA | GAT | TAC | TGC | AAA | TGT | TAC | TGC | GAC | AAG | CAT | ACA | CGC | ATT | GAG | TAA | CTG | CAT | 840 |
| 841 | AAA | TAC | AAA | AAT | GCA | TCA | TGA | TGA | AAA | ACC | GCA | AAA | ATA | AAA | GCA | AAA | TGG | CAT | AAA | 900 |
| 901 | GTA | CTA | TGC | AAA | AAA | GGG | TGT | TAT | ATT | TCC | AAA | TCC | CTA | AAT | TGA | AGA | CAT | GAG | CCA | 960 |
| 961 | AAA | GTG | GAA | ACC | CGA | CTT | C 3' | | | | | | | | | | | | | | or fragments thereof which encode proteins having the enzymatic activity of esterase D.

8. An esterase cDNA nucleotide sequence coding for a polypeptide having the following amino acid sequence:

| Pos | | | | | | | | | | | | | | | | | | | | | Pos |
|---|---|---|---|---|---|---|---|---|---|---|---|---|---|---|---|---|---|---|---|---|---|
| 1 | | | | Val | Phe | Glu | Met | Ala | Leu | Lys | Gln | Ile | Ser | Ser | Asn | Lys | Cys | Phe | Gly | Gly | Leu | Gln | Lys | 17 |
| 18 | Pro | Lys | Ala | His | Asp | Ser | Val | Glu | Leu | Asn | Cys | Lys | Met | Lys | Phe | Ala | Val | Tyr | Leu | Pro | 37 |
| 38 | Glu | Gln | Asn | Glu | Thr | Gly | Lys | Cys | Pro | Ala | Leu | Tyr | Trp | Leu | Ser | Gly | Leu | Thr | Cys | Thr | 57 |
| 58 | Val | Ile | Ala | Phe | Pro | Ser | Ser | Gly | His | Gln | Ser | Lys | Ser | Ala | Ser | Glu | His | Gly | Leu | Val | 77 |
| 78 | Asp | Phe | Gly | Pro | Asp | Thr | Pro | Arg | Ile | Gly | Cys | Lys | Ile | Gly | Asp | Pro | Asn | Glu | Ser | Trp | 97 |
| 98 | Tyr | Arg | Met | Thr | Gly | Val | Phe | Tyr | Val | Ala | Thr | Glu | Asp | Trp | Lys | Asn | Ala | Lys | Thr | Asn | 117 |
| 118 | Val | Asp | Pro | Tyr | Ser | Ser | Tyr | Glu | Gly | Leu | Gln | Leu | Ile | Gly | Pro | His | Ala | Phe | Leu | Pro | 137 |
| 138 | Pro | Ala | Leu | Gln | Arg | Ile | Met | Gly | Phe | His | Ser | Gly | Gly | Ala | Gly | Ile | Ile | Leu | Ile | 157 |
| 158 | Cys | Val | Leu | Lys | Asn | Pro | Tyr | Lys | Tyr | Ala | Ser | Val | Lys | Gly | Pro | Ala | Gly | Phe | Cys | Asn | 177 |
| 178 | Pro | Leu | Lys | Cys | Pro | Trp | Ser | Lys | Pro | Ser | Ser | Gly | Tyr | Leu | Phe | Pro | Gly | Gly | Gln | Ser | 197 |
| 198 | Lys | Ile | Ala | Tyr | Asp | Lys | Thr | His | Lys | Leu | Tyr | Lys | Val | Gln | Lys | Thr | Ser | Gln | Leu | Asp | 217 |
| 218 | Ile | Phe | Asp | Gln | Ala | Gly | Leu | Asp | Lys | Phe | Leu | Asp | Gly | Arg | Leu | Pro | Glu | Asp | 237 |
| 238 | Asn | Asp | Ala | Ala | Ser | Cys | Thr | Glu | Lys | Thr | Val | Phe | Ile | Val | Phe | Ile | Gln | Leu | Gly | Asp | 257 |
| 258 | Tyr | Tyr | Ser | Tyr | Gly | Asp | Lys | Ala | Phe | Thr | Asp | His | Arg | His | His | Gly | 277 |
| 278 | Lys | Asn | Ala | — | | | | | | | | | | | | | | | | | | | or a fragment thereof which encodes a protein having the enzymatic activity of esterase D.

9. A human esterase D cDNA probe comprising the nucleotide sequence of claim 10, which sequence is radioactivity labelled.

10. The probe of claim 7 which is radioactively labeled with $^{32}P$.

11. An oligonucleotide probe labeled with $^{32}P$ and which is complementary to the human esterase D DNA or a hybridizable portion thereof.

* * * * *

UNITED STATES PATENT AND TRADEMARK OFFICE
CERTIFICATE OF CORRECTION

PATENT NO. : 5,011,773
DATED : 4/30/91
INVENTOR(S) : Lee et al

It is certified that error appears in the above-identified patent and that said Letters Patent is hereby corrected as shown below:

On the title page, item [73] Assignee: delete "Reagents" and substitute therefor --Regents--.

Column 8, line 53, delete "RM" and substitute therefor --RB--.

Column 20, line 16, after "(I bid)" delete "," and substitute therefor --.--.

Column 20, line 17, delete "Eagle s" and substitute therefor --Eagle's--.

Column 29, line 5, delete "10" and substitute therefor --7--;
line 5, delete "radioactivity" and substitute therefor --radioactively--; and
line 5, delete "sequenceis" and therefor substitute therefor --sequences is--.

Column 30, line 1, delete "7" and substitute therefor --9--.

Signed and Sealed this

Seventeenth Day of November, 1992

Attest:

DOUGLAS B. COMER

Attesting Officer          Acting Commissioner of Patents and Trademarks